United States Patent
Huwais

(10) Patent No.: US 9,326,778 B2
(45) Date of Patent: May 3, 2016

(54) AUTOGRAFTING OSTEOTOME

(71) Applicant: Huwais IP Holding LLC, Jackson, MI (US)

(72) Inventor: Salah Huwais, Jackson, MI (US)

(73) Assignee: Huwais IP Holding LLC, Jackson, MI (US)

( * ) Notice: Subject to any disclaimer, the term of this patent is extended or adjusted under 35 U.S.C. 154(b) by 0 days.

(21) Appl. No.: 14/611,452

(22) Filed: Feb. 2, 2015

(65) Prior Publication Data
US 2015/0150565 A1 Jun. 4, 2015

Related U.S. Application Data

(63) Continuation of application No. PCT/US2013/055539, filed on Aug. 19, 2013, and a continuation-in-part of application No. 13/608,307, filed on Sep. 10, 2012, now Pat. No. 9,028,253, which
(Continued)

(51) Int. Cl.
*A61C 8/00* (2006.01)
*A61B 17/16* (2006.01)
(Continued)

(52) U.S. Cl.
CPC ............ *A61B 17/1615* (2013.01); *A61C 8/0089* (2013.01); *A61B 17/1635* (2013.01); *A61B 17/885* (2013.01); *A61B 2017/320008* (2013.01); *A61B 2017/320072* (2013.01)

(58) Field of Classification Search
CPC .......... A61C 3/02; A61C 8/00; A61C 8/0089; A61B 17/1615; A61B 17/320068; A61B 17/1635; A61B 17/1604; A61B 17/885; A61B 2017/320072; A61B 2017/320012; A61B 2017/32008; A61B 17/16
See application file for complete search history.

(56) References Cited

U.S. PATENT DOCUMENTS 3,556,669 A 1/1971 Valeska et al.
D269,040 S 5/1983 Deemer
(Continued)

FOREIGN PATENT DOCUMENTS

DE 102004010859 A 4/2005
DE 102004010856 A 6/2005
(Continued)

OTHER PUBLICATIONS

Anitua, Ridge expansion with motorized drills, Implant Dialogue, 14 pgs.
(Continued)

*Primary Examiner* — Edward Moran
(74) *Attorney, Agent, or Firm* — Endurance Law Group, PLC

(57) ABSTRACT

A fluted osteotome is rotated in one direction to enlarge an osteotomy by burnishing, and by cutting/drilling when turned in an opposite direction. A conically tapered body has an apical end with lips. The lips are set to grind bone when rotated in the burnishing direction and cut bone when turned in the cutting/drilling direction. Helical flutes and interposed lands are disposed about the body. The flutes each have a working edge that burnishes bone when rotated in the burnishing direction and cuts bone when turned in the cutting/drilling direction. The lips and lands generate an opposing axial reaction force that improves surgical control. The osteotome auto-grafts bone by reapplying ground particles in a compacted manner along the entire depth of the osteotomy, particularly at the bottom.

15 Claims, 20 Drawing Sheets

Related U.S. Application Data is a continuation-in-part of application No. 13/427,391, filed on Mar. 22, 2012, now Pat. No. 9,022,783.

(60) Provisional application No. 61/727,849, filed on Nov. 19, 2012, provisional application No. 61/466,579, filed on Mar. 23, 2011.

(51) Int. Cl.
  *A61B 17/32* (2006.01)
  *A61B 17/88* (2006.01)

(56) References Cited

U.S. PATENT DOCUMENTS

| | | | |
|---|---|---|---|
| 4,474,556 A | 10/1984 | Ellis et al. | |
| 4,850,867 A | 7/1989 | Senia et al. | |
| 5,220,964 A | 6/1993 | Deken et al. | |
| 5,443,468 A | 8/1995 | Johnson | |
| 5,667,509 A | 9/1997 | Westin | |
| 5,688,120 A | 11/1997 | Yacker et al. | |
| 5,735,689 A | 4/1998 | Mcspadden | |
| 6,146,138 A | 11/2000 | Dalmau | |
| 6,179,616 B1 * | 1/2001 | Danger | A61C 3/02 433/165 |
| 6,186,787 B1 | 2/2001 | Danger et al. | |
| 6,641,395 B2 | 11/2003 | Kumar et al. | |
| 7,198,488 B2 * | 4/2007 | Lang et al. | 433/174 |
| 7,241,144 B2 | 7/2007 | Nilo et al. | |
| 7,247,020 B2 | 7/2007 | Takahashi et al. | |
| 7,300,281 B2 | 11/2007 | Cantatore et al. | |
| 7,402,040 B2 | 7/2008 | Turri | |
| 7,435,086 B2 | 10/2008 | Berutti et al. | |
| 7,547,210 B1 | 6/2009 | Valen | |
| D611,511 S | 3/2010 | Anitua Aldecoa | |
| 7,766,657 B2 | 8/2010 | Jaunberzins | |
| 2001/0019816 A1 | 9/2001 | Kumar | |
| 2002/0094508 A1 | 7/2002 | Lorenzi | |
| 2005/0123364 A1 | 6/2005 | Zhou | |
| 2005/0273110 A1 | 12/2005 | Boehm, Jr. et al. | |
| 2006/0085005 A1 | 4/2006 | Kenealy et al. | |
| 2006/0111724 A1 * | 5/2006 | Yeung Wai Ping | A61B 17/1635 606/80 |
| 2006/0121415 A1 | 6/2006 | Anitua Aldecoa | |
| 2006/0127847 A1 | 6/2006 | Danger et al. | |
| 2006/0210949 A1 | 9/2006 | Stoop | |
| 2007/0037117 A1 | 2/2007 | Jaunberzins | |
| 2010/0266984 A1 | 10/2010 | Jung | |
| 2010/0273128 A1 | 10/2010 | Anitua Aldecoa | |
| 2010/0291511 A1 | 11/2010 | Lee | |
| 2010/0297578 A1 | 11/2010 | Jaunberzins | |
| 2012/0244497 A1 | 9/2012 | Huwais | |
| 2013/0218160 A1 * | 8/2013 | Bjorn | A61B 17/1695 606/80 |

FOREIGN PATENT DOCUMENTS

| | | |
|---|---|---|
| DE | 102004010858 A | 6/2005 |
| DE | 102004010860 A | 6/2005 |
| EP | 0379201 A | 7/1990 |
| EP | 2119403 A1 | 11/2009 |
| FR | 2594684 A | 8/1987 |
| JP | 10217030 A | 8/1998 |
| JP | H10217030 | 8/1998 |
| WO | 2005011514 A | 2/2005 |

OTHER PUBLICATIONS

Biomet Sports Medicine, Bone Dowel Harvester, Copyright 2007, Biomet Sports Medicine, Inc., PO Box 587, Warsaw, IN 46581-0587 (www.biometsportsmedicine.com).

Calvo-Guarado JL et al., "Compressive osteotomes for expansion and maxilla sinus floor lifting," Med Oral Patol Oral Cir Bucal 2006; 11:E52-5.

Lee, Atraumatic Ridge Expansion and Implant Site Preparation with Motorized Bone Expanders, Practical Procedures and Aesthetic Dentistry 2006; 18(1): pp. A-F.

Nishioka, Bone Spreading Technique (Dec. 9, 2010), retrieved Mar. 10, 2012 from www.dentistrytoday.com/implants/4228-bone-spreading-technique, pp. 1-4.

Oxforddictionaries.com. Definition of radial [retrieved on Feb. 25, 2015]. Retrieved from the Internet:http://www.oxforddictionaries.com/us/definition/american_english/radial.

Anitua, Ridge expansion with motorized expander drills, Implant Dialogue, 14 pgs.

Biohorizons, VIP Catalog and Surgical Manual, 2008, 28 pgs.

Biomet Sports Medicine, Bone Dowel Harvester, Copyright 2007, Biomet Sports Medicine, Inc., P.O. Box 587, Warsaw, IN 46581-0587 (www.biometsportsmedicine.com).

Calvo-Guirado JL et al. "Compressive osteotomes for expansion and maxilla sinus floor lifting," Med Oral Patol Oral Cir Bucal 2006;11:E52-5.

Goyal et al., Bone Manipulation Techniques, International Journal of Clinical Implant Dentistry, Jan.-Apr. 2009; 1(1): pp. 22-31.

Meisinger, Bone Management catalog, pp. 161-178.

Meisinger, Split-Control, retrieved Mar. 10, 2012 from www.bone-management.com/eng/bm_sortimente_anw_split_eng.htm.

Steier et al., Better horizontal ridge expansion, Dental Tribune I, Sep. 22-28, 2008, pp. 9-10.

Summers, A New Concept in Maxillary Implant Surgery: The Osteotome Technique, Compend Contin Educ Dent, vol. XV, No. 2, pp. 152-160.

www.dentsply-friadent.com, "Ankylos Surgical Manual."

www.nobelbiocare.com, "Validating Innovation: NobelActive Technical and Clinical Story," Nobel Biocare Services AG, 2011.

* cited by examiner

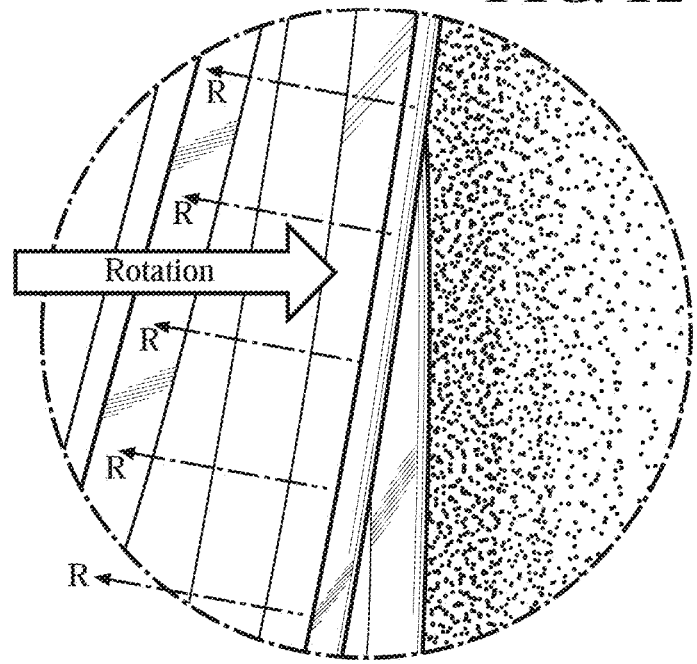
FIG. 12
FIG. 13
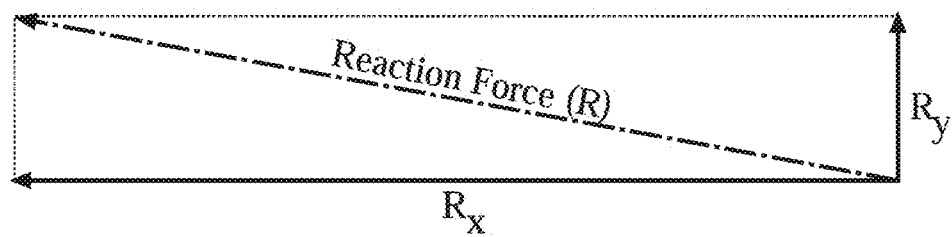

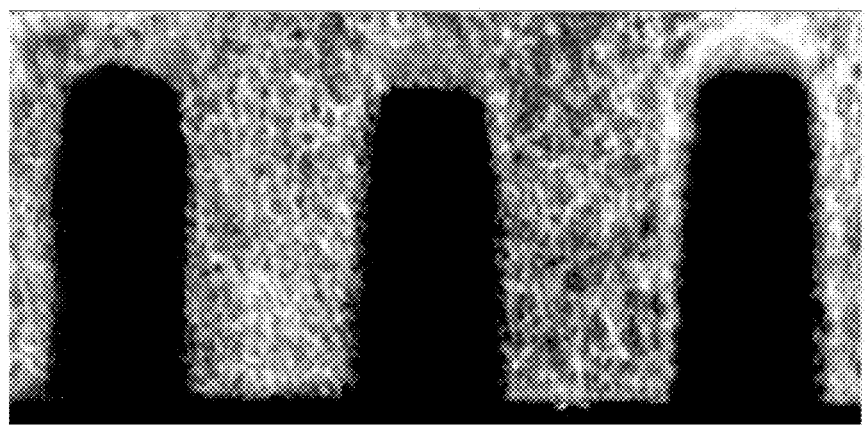
FIG. 22
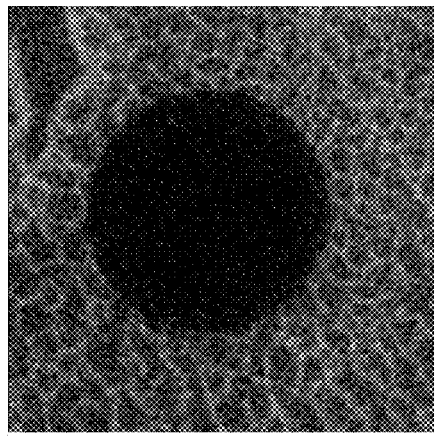 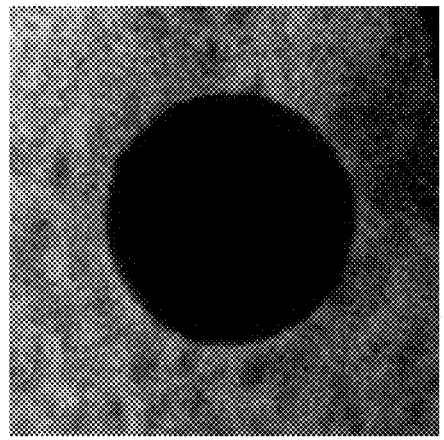
FIG. 23A  FIG. 23B
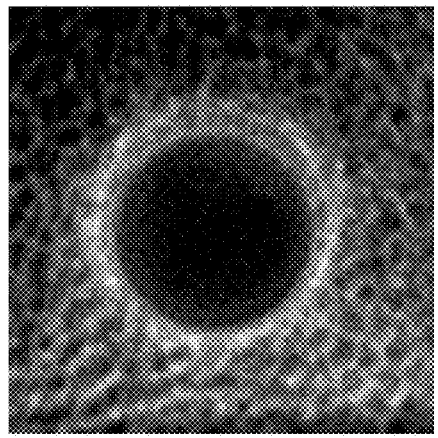 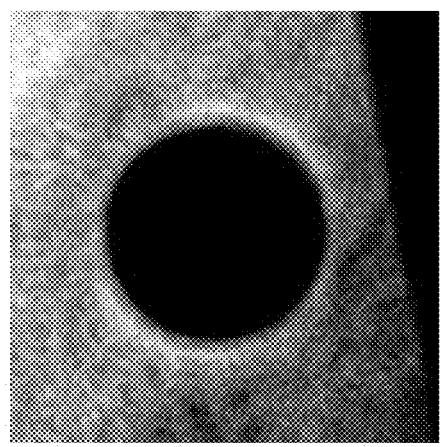
FIG. 23C  FIG. 23D

AUTOGRAFTING OSTEOTOME

CROSS REFERENCE TO RELATED APPLICATIONS

This application is a Continuation of PCT/US13/55539, filed Aug. 19, 2013, published as WO 2014/077920, which in turn claims priority to Provisional Patent Application No. 61/727,849 filed Nov. 19, 2012. This application is also a continuation-in-part of U.S. Ser. No. 13/608,307 filed Sep. 10, 2012, published as US 2013/0004918, which is a continuation-in-part of U.S. Ser. No. 13/427,391 filed Mar. 22, 2012, published as US 2012/0244497, which claims priority to Provisional Patent Application No. 61/466,579 filed Mar. 23, 2011. The entire disclosures of each priority document are hereby incorporated by reference and relied upon.

BACKGROUND OF THE INVENTION

1. Field of the Invention

The invention relates generally to tools for preparing a hole to receive an implant or fixture, and more particularly to rotary osteotomes and methods implemented thereby for expanding an osteotomy or hole in cellular material to receive an implant or other fixation device.

2. Description of Related Art

An implant is a medical device manufactured to replace a missing biological structure, to support a damaged biological structure, or to enhance an existing biological structure. Bone implants are implants of the type placed into the bone of a patient. Bone implants may be found throughout the human skeletal system, including dental implants in a jaw bone to replace a lost or damaged tooth, joint implants to replace a damaged joints such as hips and knees, and reinforcement implants installed to repair fractures and remediate other deficiencies, to name but a few. The placement of an implant often requires a preparation into the bone using either hand osteotomes or precision drills with highly regulated speed to prevent burning or pressure necrosis of the bone. After a variable amount of time to allow the bone to grow on to the surface of the implant (or in some cases to a fixture portion of an implant), sufficient healing will enable a patient to start rehabilitation therapy or return to normal use or perhaps the placement of a restoration or other attachment feature.

In the example of a dental implant, preparation of a hole or osteotomy is required to receive a bone implant. According to current techniques, at edentulous (without teeth) jaw sites that need expansion, a pilot hole is bored into the recipient bone to form the initial osteotomy, taking care to avoid the vital structures. The pilot hole is then expanded using progressively wider expander devices called osteotomes, manually advanced by the surgeon (typically between three and seven successive expanding steps, depending on implant width and length). Once the receiving hole has been properly prepared, a fixture screw (usually self-tapping) is screwed into place at a precise torque so as not to overload the surrounding bone.

The osteotome technique has become widely utilized in certain situations requiring preparation of an osteotomy site by expansion of a pilot hole. By nature, the osteotome technique is a traumatic procedure. Osteotomes are traditionally not rotating devices but rather advanced with the impact of a surgical mallet, which compacts and expands the bone in the process of preparing osteotomy sites that will allow implant placement. Treatment of a mandibular site, for example, is often limited due to the increased density and reduced plasticity exhibited by the bone in this region. Other non-dental bone implant sites may have similar challenging density and plasticity characteristics. Or, the location of the bone may be wholly unsuitable for the violent impact of an osteotome, such as in small bone applications like the vertebrae and hand/wrist areas to name a few. Additionally, since the traditional osteotome is inserted by hammering, the explosive nature of the percussive force provides limited control over the expansion process, which often leads to unintentional displacement or fracture such as in the labial plate of bone in dental applications. Many patients do not tolerate the osteotome technique well, frequently complaining about the impact from the surgical mallet. In addition, reports have documented the development of a variety of complications that result from the percussive trauma in dental applications, including vertigo and the eyes may show nystagmus (i.e., constant involuntary cyclical movement of the eyeball in any direction).

More recently, alternative techniques to the hammered osteotome have been developed for bone applications that allow for less traumatic preparation of implant sites. These alternative procedures are based on the use of motor-driven screw-type bone expanders, such as those marketed by Meisinger (Neuss, Germany). First a pilot hole is drilled at the implant site, then a series of progressively larger expander screw taps are introduced into the bone by hand or with motor-driven rotation, which decreases surgical trauma (as compared with hammer taps) while providing some degree of control over the expansion site. The thread pattern of the expander screw taps is intended to compact bone laterally as the expander tap advances into the osseous crest. This system allows expansion and preparation of implant sites in Type II and III bone, as well as compaction of Type IV bone.

US Publication No. 2006/0121415 to Anitua Aldecoa describes the use of motor-driven tools and methods for expanding a human bone for the purpose of installing a dental implant. Similar to the progressive illustration described above, a starter drill is used to create a pilot hole followed by the insertion of an expander screw tap type osteotome having a conical/cylindrical geometry with progressive cross-section. A surgical motor is used to rotate the osteotome at relatively low speeds. Another example of this technique is described in U.S. Pat. No. 7,241,144 to Nilo et al, issued Jul. 10, 2007. The entire disclosures of US Publication No. 2006/0121415 and U.S. Pat. No. 7,241,144 are hereby incorporated by reference.

U.S. Pat. No. 7,402,040 to Turri, issued Jul. 22, 2008, discloses a hybrid hammered and rotary osteotome technique using a non-circular osteotome design. In the preferred embodiment, the non-circular osteotome is first hammered to the bottom of the osteotomy, and then when at full depth rotated back-and-forth by hand to achieve a final expansion shape. In an alternative embodiment however, impulse hammering and rotation are concurrently applied in order to drive the osteotome deeper into the osteotomy, which advance into the osteotomy is encouraged by helical edges that generate "a tractive force that tends to advance it [the osteotome] towards the interior of the osseous site". (Turri at Column 9, lines 42-43.) In other words, Turri's alternative embodiment osteotome uses screw threads in combination with percussive hammering and powered rotation to pull the osteotome down into the osteotomy.

In the prior art designs involving motor-driven bone expansion, including those of Anitua Aldecoa, Niro and Turri described above, the rotary speed of the expander screw tap is locked in a fixed relationship to the expansion rate of the osteotomy. This is because threads on the expander device cut into the bone and "pull" the expander tap deeper into the initial osteotomy with rotation. Axial advance is thus controlled by pitch of threads and rotation speed; the thread pitch of the expander is fixed and cannot be altered on-the-fly by the surgeon. If a surgeon wishes to expand the bone more slowly, the only recourse is to turn the expander more slowly. Conversely, if the surgeon wishes to expand the bone more rapidly, the only option is to turn the expander tool more quickly. Thus, the rate of bone expansion is a direct and unalterable function of the rate at which the surgeon turns the expander tool, and the surgeon is unable to vary other parameters such as pressure and/or rotation rate to achieve an optimum expansion rate.

This inexorable linking of tool rotation rate to bone expansion rate in all prior art rotary expander systems limits surgical control over the implant process, and in some cases may lead to unnecessary patient discomfort. There is therefore a need in the art for an improved surgical method for expanding an osteotomy to receive an implant in all bone applications, and tools therefor, that provide greater surgical control, are less costly, less likely to introduce error and that reduce patient discomfort.

Another area of interest with respect to preparing bone to receive an implant or fixation screw is the subsequent osseointegration of the implant. The direct structural and functional connection between living bone and the surface of a load-bearing artificial implant leads to enhanced overall success of the surgical procedure for the patient. Current approaches to improving the direct contact of bone and implant surface are directed toward the use of engineered cements and/or proprietary implant surfaces that typically include porous construction. The porous properties of the implant surface contribute to extensive bone infiltration, allowing osteoblast activity to take place. In addition, the porous structure allows for soft tissue adherence and vascularization within the implant. One significant disadvantage of the current approaches to improving osseointegration, namely the use of cements and implant constructions, is the relatively high added cost. The cements and engineered implants tend to be proprietary products marketed at premium prices. For example, it is not uncommon for a single bone screw used in a standard fixation application to cost $5000 (USD).

There is therefore a need for improved tools and techniques that facilitate osseointegration without the attendant high cost associated with present cements and engineered implants.

Furthermore, other types of non-organic cellular materials, such as metal foams used in some aerospace applications, also require fixation techniques that may benefit from the hole preparation concepts used in the medical field for preparing bone.

BRIEF SUMMARY OF THE INVENTION

According to one aspect of this invention, a rotary osteotome is configured to be turned in one direction to enlarge an osteotomy by burnishing. The rotary osteotome includes a shank having an elongated cylindrical shaft. A body joined is to the shank. The body has an apical end remote from the shank, and a conically tapered profile decreasing from a maximum diameter adjacent the shank to a minimum diameter adjacent the apical end. The apical end includes at least one lip. A plurality of flutes are disposed about the body. Each flute has a burnishing face and an opposing cutting face. A land is formed between adjacent flutes. The lip is configured to simultaneously auto-graft and compact bone (i.e., gently push osseous structure laterally outwardly in a condensation mechanism) when continuously rotated at high speed in a burnishing direction and concurrently forcibly advanced into an osteotomy. The auto-grafting and compaction action of the lip enable the rotary osteotome to expand an osteotomy from top to bottom in a progressive manner while retaining the beneficial properties of immediately grafting displaced bone material directly into the osteotomy, and thereby promoting osseointegration of a subsequently placed implant or fixation member.

According to another aspect of this invention, a rotary tool is configured to be turned continuously in one direction to enlarge a hole in cellular material (i.e., not limited to bone) by burnishing. The rotary tool includes a shank that establishes a longitudinal axis of rotation for the rotary tool. A body is joined to the shank. The body has an apical end remote from the shank, and a conically tapered profile decreasing from a maximum diameter adjacent the shank to a minimum diameter adjacent the apical end. The apical end includes at least one lip. A plurality of flutes are disposed about the body. Each flute has a burnishing face and an opposing cutting face. A land is formed between adjacent flutes. Each land has a land face joining a burnishing face of one the flute and a cutting face of an adjacent flute. At least one of the lip and the lands are configured to generate an opposing axial reaction force when continuously rotated in a burnishing direction and concurrently forcibly advanced into a hole. The push-back phenomenon gives the user enhanced control over the expansion procedure, and effective decouples the rotation of the tool to the rate of expansion of the hole.

These and other aspects of the invention will be understood more fully by considering the detailed description and illustrations of this invention.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 12 is an enlarged view of the area circumscribed at 12 in FIG. 11 and enhanced with reaction forces (R) as applied by the walls of the bone to the rotary osteotome in response to rotation of the osteotome in the burnishing direction;

FIG. 13 is a diagram of the reaction forces (R) of FIG. 12, shown broken into component lateral ($R_x$) and axial ($R_y$) forces;

FIG. 22 is a micro-CT image developed during testing of a prototype rotary osteotome according to this invention, and showing a transverse slice through a Porcine03 medial tibial plateau with comparative holes created by: (A-left) a prior art burr drill, (B-center) the rotary osteotome of this invention rotated in a cutting direction, and (C-right) the rotary osteotome of this invention rotated in a burnishing direction;

FIGS. 23A-D are micro-CT images developed during testing of a prototype rotary osteotome according to this invention, and showing comparative axial slice views of Porcine03 medial tibial plateau holes created with a prior art burr drill (FIG. 23A) and the rotary osteotome of this invention rotated in a burnishing direction (FIG. 23C), and comparative axial slice views of average bone mineral density projection of 1 cm volume around Porcine02 medial holes created with a prior art burr drill (FIG. 23B) and the rotary osteotome of this invention rotated in a burnishing direction (FIG. 23D);

DETAILED DESCRIPTION OF THE INVENTION

Figure 1:
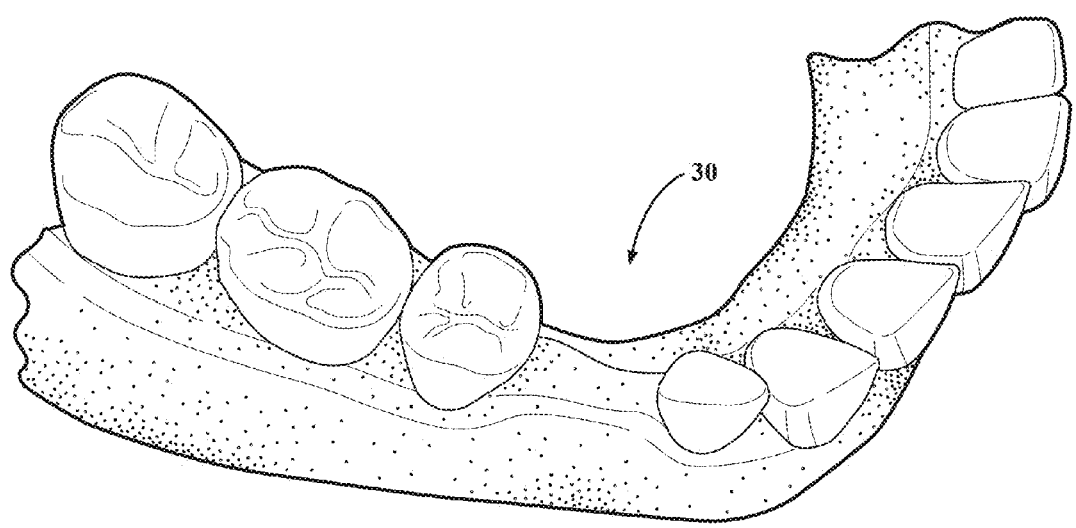
FIG. 1 depicts an exemplary application of the present invention at an edentulous (without teeth) jaw site that needs expansion to receive an implant.
Figure 2:
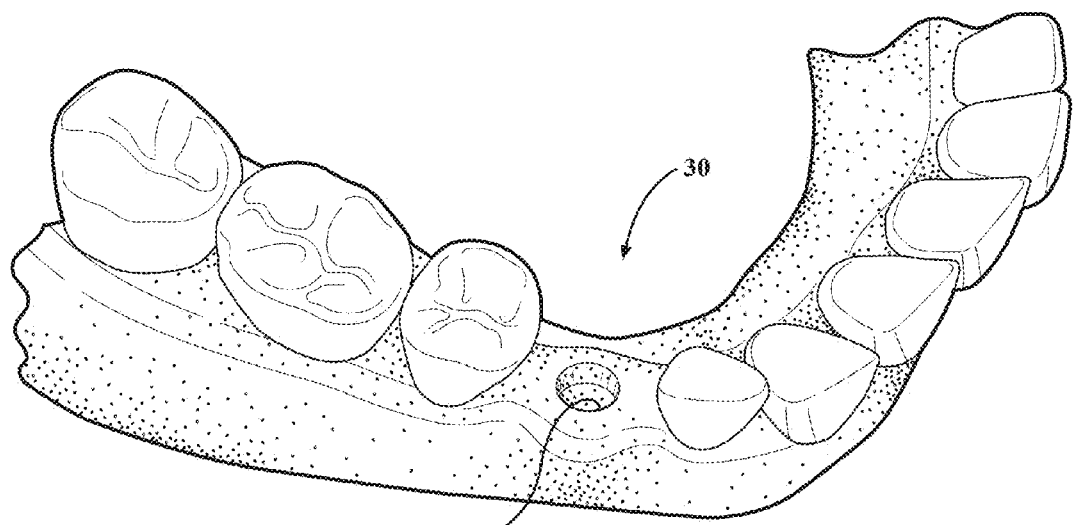
FIG. 2 is a view as in FIG. 1, but showing the resulting fully prepared osteotomy as achieved through use of the present invention in a progressive series of expansion steps.
Figure 3:
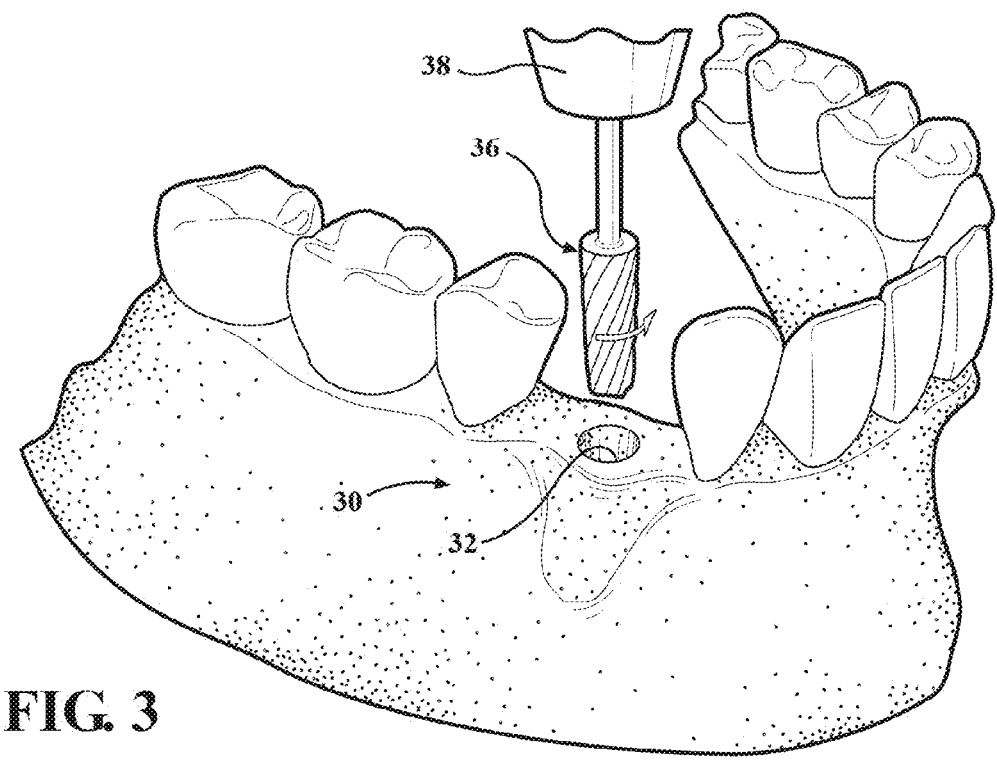
FIG. 3 is a view as in FIG. 1 showing a progressive expansion step with a rotary osteotome according to one embodiment of this invention.
Figure 4:
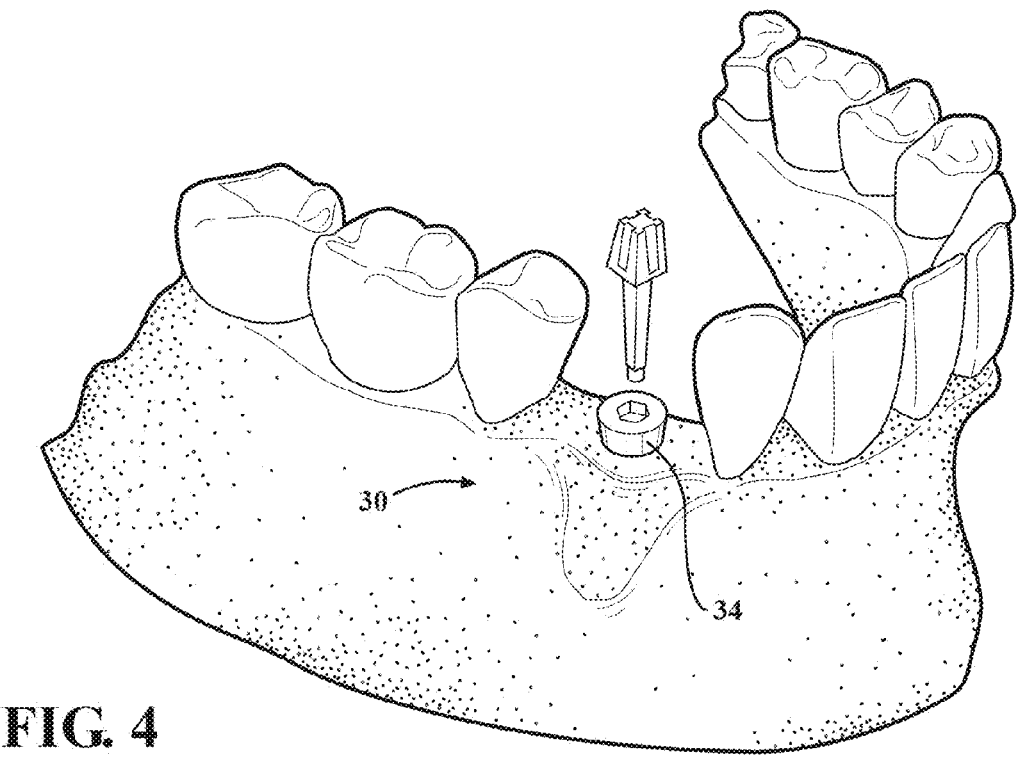
FIG. 4 is a view as in FIG. 2 in which an installed implant is poised to receive an abutment or base for subsequent prosthetic (not shown)

Referring to the figures, wherein like numerals indicate like or corresponding parts throughout the several views, FIGS. 1-4 show the example of a dental implant, in which preparation of an osteotomy is required to receive a bone implant (FIG. 4). It will be understood that this invention is not limited to dental applications, but may be applied across a wide spectrum of orthopedic applications. Furthermore, the invention is not even limited to bone or orthopedic applications, but may be used to prepare holes in metal foam and other cellular materials for industrial and commercial applications, to name but a few. In FIG. 1, an edentulous (without teeth) jaw site 30 is shown that needs expanded and prepared as an osteotomy 32 (FIG. 2) in order to receive an implant 34 (FIG. 4) or other fixture device. The series of steps include first boring a pilot hole into the recipient bone to form the initial osteotomy (not shown), then incrementally expanding the osteotomy using progressively wider rotary expander devices or osteotomes, generally indicated at 36, as shown in FIG. 3. Once the osteotomy has been prepared, the implant 34 or fixture screw is screwed into place as illustrated in FIG. 4. The procedure of forming an osteotomy is described, generally, in US 2013/0004918 published Jan. 3, 2013 to Huwais, the entire disclosure of which is hereby incorporated by reference.

Figure 5:
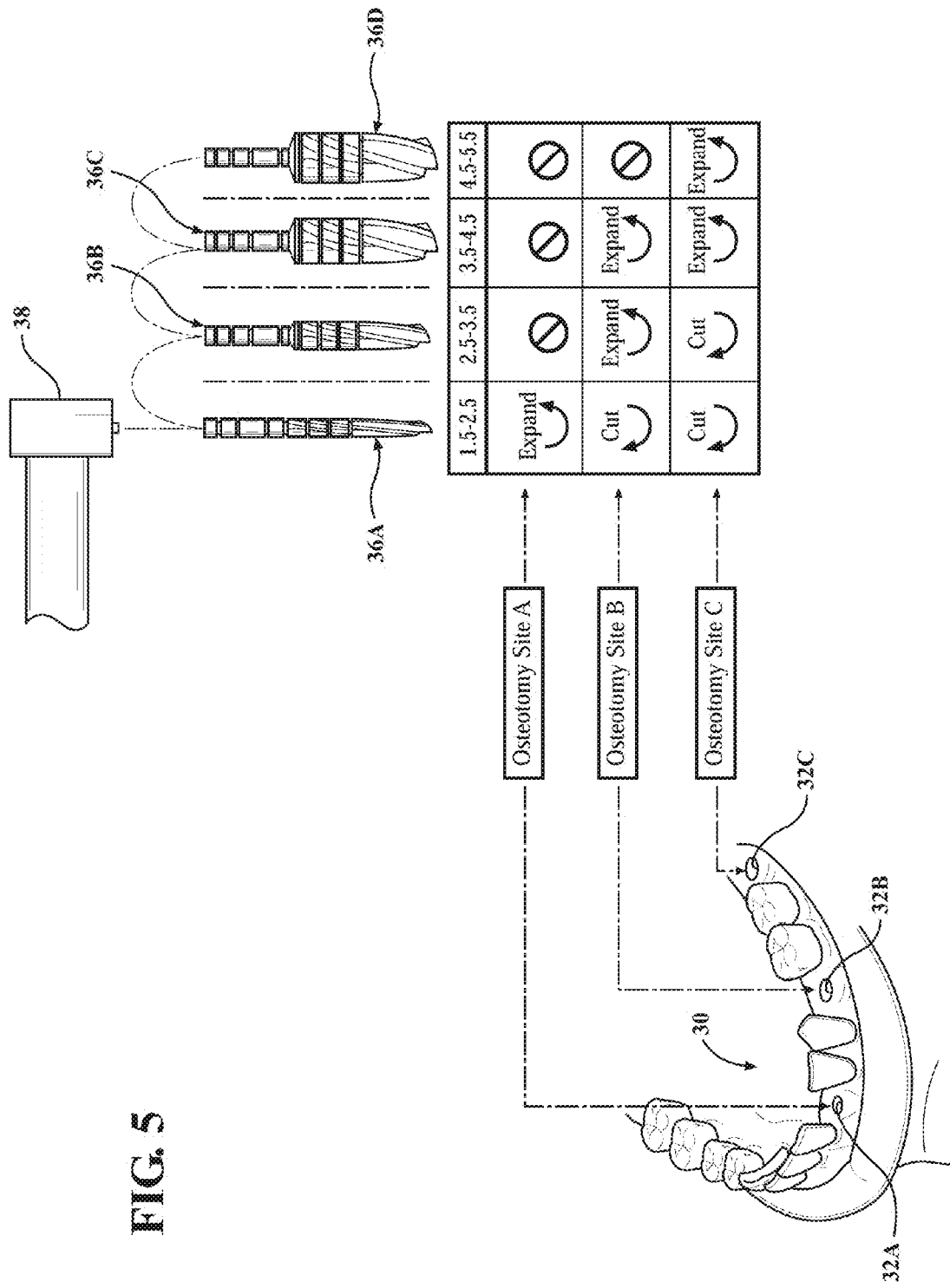
FIG. 5 is a diagrammatic view illustrating by way of example the use of a surgical kit containing four osteotomes of progressively larger diameter according to the present invention in combination with a reversible drill motor to concurrently prepare three separate osteotomy sites in a human jaw using selective reversal of osteotome direction to enlarge each osteotomy either by cutting or burnishing without removing the osteotome from the surgical drill motor.

FIG. 5 is a diagrammatic view illustrating by way of example the use of a surgical kit containing four osteotomes 36A-D of progressively larger diameter according to the present invention in combination with a reversible surgical drill motor 38 to concurrently prepare three separate osteotomy sites 32A, 32B and 32C, respectively, in a human jaw bone 30 using selective reversal of osteotome direction to enlarge each osteotomy either by cutting or burnishing without removing a given osteotome 36 from the surgical drill motor 38. Although the example is presented here again in the context of a dental application, those of skill in the art will appreciate that the described techniques are adaptable to non-dental applications including, but not limited to, joint replacement, bone fixations generally and foam metals (see for example FIGS. 27B and 28).

Returning to the example of FIG. 5, a first osteotomy site 32A is located in the front of the mandible bone 30 where the bone width is relatively narrow. The composition of the bone 30 in the region of the first osteotomy site 32A may be described as predominantly Type II. A second osteotomy site 32B is located slightly posterior of the first site 32A in a region of the mandible that has moderate bone 30 width. The composition of the bone 30 in the region of the second osteotomy site 32B may be described as generally a combination of Types II and III. A third osteotomy site 32C is located in a molar region of the mandible and is surrounded by a relatively generous bone 30 width. The composition of the bone 30 in the region of the third osteotomy site 32C may be described as predominantly Type III. Due to the varying width and composition of bone 30 at sites 32A, 32B and 32C, the surgeon does not wish to apply exactly the same technique and procedure to each osteotomy 32. By using the present invention, a surgeon (or user in non-surgical applications) has the ability to concurrently prepare all three osteotomy sites 32A-32C in different ways.

In this example, each osteotomy site 32A-32C is presumed to have an initial osteotomy prepared by first drilling a pilot hole of 1.5 mm. (Of course, the circumstances of any given surgical application, whether dental or non-dental in nature, will dictate the size of initial osteotomy and other characteristics of the operation.) The surgeon locks or otherwise installs the first osteotome 36A into the drill motor 38 and sets the rotational direction to counter-clockwise. Although the surgeon may vary the rotational speed of the osteotome 36 according to the dictates of the situation in their judgment, experimental results indicate that rotation speeds between about 200-1200 RPM and torque settings between about 15-50 Ncm provide satisfactory results. More preferably rotation speeds between about 600-1000 RPM and torque settings between about 20-45 Ncm provide satisfactory results. And still more preferably, rotation speeds in the range of 800-900 RPM and torque settings of about 35 Ncm provide satisfactory results.

The surgeon then pushes the rotating first osteotome 36A into the first osteotomy site 32A to expand through burnishing (the details of which are described in detail below). However, due to the different compositional nature of the second 32B and third 32C osteotomy sites, the surgeon chooses to enlarge by cutting rather than burnishing. To affect this, the surgeon reverses the rotational direction of the drill motor 38 to clockwise without removing the first osteotome 36A from the drill motor 38. Then, using a similar pushing motion, the surgeon enlarges the second 32B and third 32C osteotomy sites by removing bone material which may, if desired, be harvested.

At this stage in the hypothetical example, the first osteotomy site 32A has been expanded as much as the surgeon desires; no further expansion is needed of the first osteotomy site 32A. However, the second 32B and third 32C osteotomy sites both require additional expansion. The surgeon then installs the second osteotome 36B into the drill motor 38 and sets the rotational direction to counter-clockwise. Skipping the completed first osteotomy site 32A, the surgeon then expands the second osteotome 36B into the second osteotomy site 32B through burnishing. Due to the different compositional nature of the third osteotomy site 32C, the surgeon chooses to enlarge by cutting rather than burnishing. To affect this, the surgeon sets the rotational direction of the surgical motor 38 to clockwise without removing the second osteotome 36B from the surgical motor 38. Then, using a similar pushing motion, the surgeon enlarges the third osteotomy site 32C by removing bone material (which may, if desired, be harvested).

Once the remaining two osteotomy sites 32B, 32C have been enlarged by the second osteotome 36B, the surgeon locks or otherwise installs the third osteotome 36C into the drill motor 38 and sets the rotational direction to counter-clockwise. Again skipping the completed first osteotomy site 32A, the second 32B and third 32C osteotomy sites are enlarged by burnishing. In both cases, the surgical motor 38 is set to turn in the counter-clockwise direction. The second osteotomy site 32B has now been expanded as much as the surgeon desires; no further expansion is needed of the second osteotomy site 32C. However, the third osteotomy site 32C still requires additional expansion. Therefore, the surgeon installs the fourth osteotome 36D into the drill motor 38 and sets the rotational direction to counter-clockwise. Skipping the completed first 32A and second 32B osteotomy sites, the third 32C osteotomy site is enlarged by burnishing using the previously described techniques. Implants 34 (or fixture portions of implants) can now be installed at each osteotomy site 32A-32C. The surgeon places a 3.0-3.25 mm implant (not shown) into the first osteotomy site 32A, a 5.0 mm implant (not shown) into the second osteotomy site 32B, and a 6.0 mm implant (not shown) in the third osteotomy site 32C. A surgeon may thus concurrently prepare a plurality of osteotomy sites 32A, 32B, 32C . . . 32n coupled with the ability to expand one site by burnishing and another site by cutting without removing the osteotome 36 from the drill motor 38. The rotary osteotome 36 is thus configured to be turned at high speed in one direction to enlarge an osteotomy by burnishing and in an opposite direction to enlarge an osteotomy by cutting.

Figure 6:
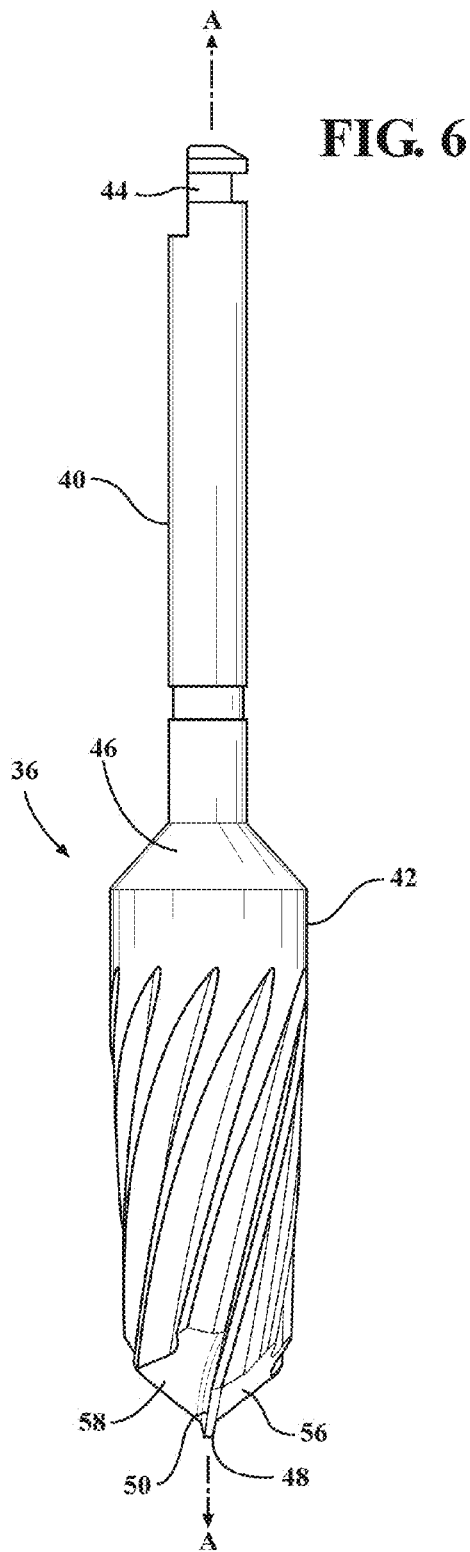
FIG. 6 is a side elevation view of a rotary osteotome according to one embodiment of this invention.

Turning now to FIG. 6, an osteotome 36 according to one preferred embodiment of this invention is shown including a shank 40 and a body 42. The shank 40 has an elongated cylindrical shaft that establishes a longitudinal axis of rotation A for the rotary osteotome 36. A drill motor engaging interface 44 is formed at the distal upper end of the shaft for connection to the drill motor 38. The particular configuration of the interface 44 may vary depending on the type of drill motor 38 used, and in some cases may even be merely a smooth portion of the shaft against which a 3- or 4-jaw collet may grip. The body 42 joins to the lower end of the shank 40, which joint may be formed with a tapered or domed transition 46. The transition 46 acts something like an umbrella as the surgeon irrigates with water during a procedure. The gentle transition 46 facilitates the flow of water (not shown) onto the osteotomy site with minimal splash or diversion, even while the osteotome 36 is spinning.

The body 42 has conically tapered profile decreasing from a maximum diameter adjacent the shank 40 to a minimum diameter adjacent an apical end 48. The apical end 48 is thus remote from the shank 40. The working length or effective length of the body is proportionally related to its taper angle and to the size and number of osteotomes (36A, 36B, 36C, 36D . . . 36n) in a kit. Preferably, all osteotomes 36 in a kit will have the same taper angle, and preferably the diameter at the upper end of the body 42 for one osteotome (e.g., 36A) is approximately equal to the diameter adjacent the apical end of the body 42 for the next larger size osteotome (e.g., 36B). Taper angles between about 1° and 5° (or more) are possible depending upon the application. More preferably taper angles between about 2°-3° will provide satisfactory results. And still more preferably, a taper angle of 2°36' is known to provide outstanding results for dental applications within the body 42 length typical requirements (e.g., ~11-15 mm).

Figure 14:
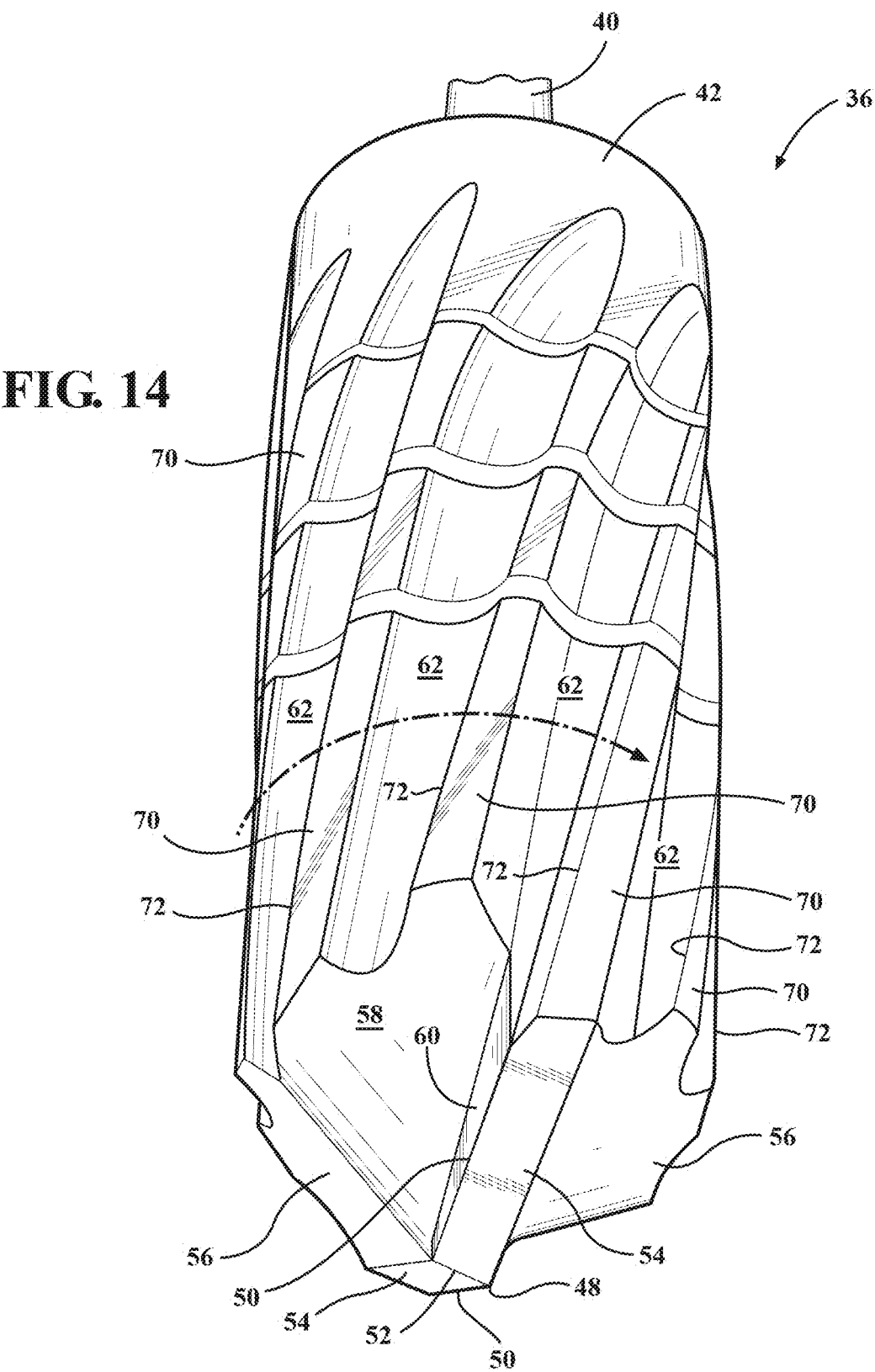
FIG. 14 is a fragmentary perspective view of the apical end of a rotary osteotome according to one embodiment of this invention.
Figure 15:
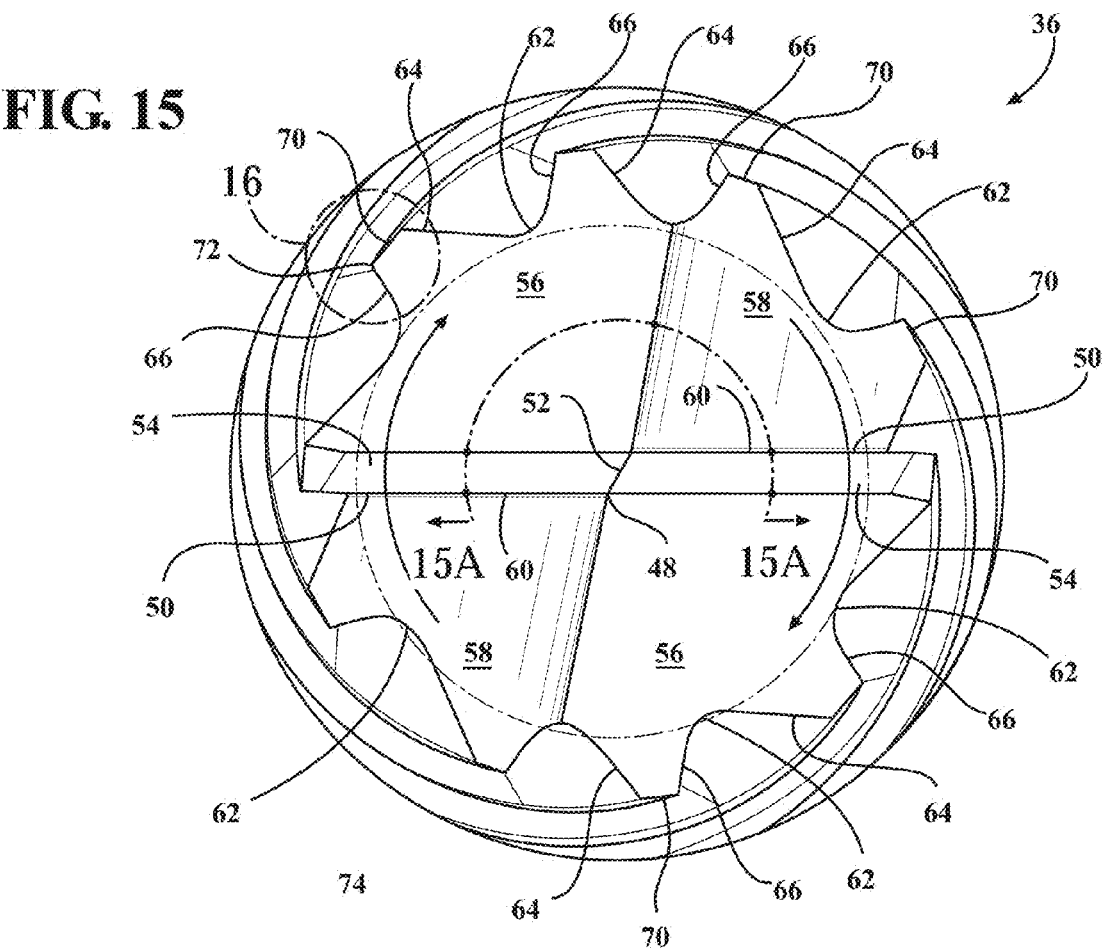
FIG. 15 is an end view of the apical end of a rotary osteotome of FIGS. 6, 10 and 14.

The apical end 48 is defined by at least one, but preferably a pair of lips 50. The lips 50 are in fact edges that are disposed on opposite sides of the apical end 48, but in the illustrated embodiment do not lie within a common plane. In other words, as shown in FIGS. 14 and 15, the lips 50 are slightly offset (in terms of a direct diametrical alignment) by the short length of a chisel point 52 extending central through the longitudinal axis A. The chisel point 52 is a common feature found in drilling tools, but alternative apical end 48 formations to the chisel point 52 are of course possible, including rounded and simple pointed shapes, etc. As mentioned, the lips 50 are edges that angle upwardly and outwardly (radially) from the apical end 48. The angle of the lips 50 may be varied to optimize performance of the particular application. In practice, the lip angle may be approximately 60° measured relative to longitudinal axis A, or 120° measured between the two opposing lips 50.

Each lip 50 has a generally planar first trailing flank 54. The first trailing flanks 54 are canted from their respective lips 50 at a first angle. The first angle may be varied to optimize performance and the particular application. In practice, the first angle may be approximately 45° measured relative to longitudinal axis A, or 90° measured between the two opposing first trailing flanks 54. It will be appreciated therefore that the two opposing first trailing flanks 54 are set in opposite directions so that when the osteotome 36 is rotated in use, the first trailing flanks 54 either lead or follow their respective lips 50. When first trailing flanks 54 lead their respective lips 50, the osteotome is said to be turning in a burnishing direction; and conversely when the first trailing flanks 54 follow their respective lips 50, the osteotome is said to be turning in a cutting direction, i.e., with the lips 50 in the lead and serving to cut or slice bone. In the burnishing direction, the first trailing flanks 54 form, in effect, a large negative rake angle for the lips 50 so as to minimize chip formation and shear deformation in the bone (or other host material) at the point of contact with the lips 50. (See for example FIGS. 17 and 20.)

Figure 10:
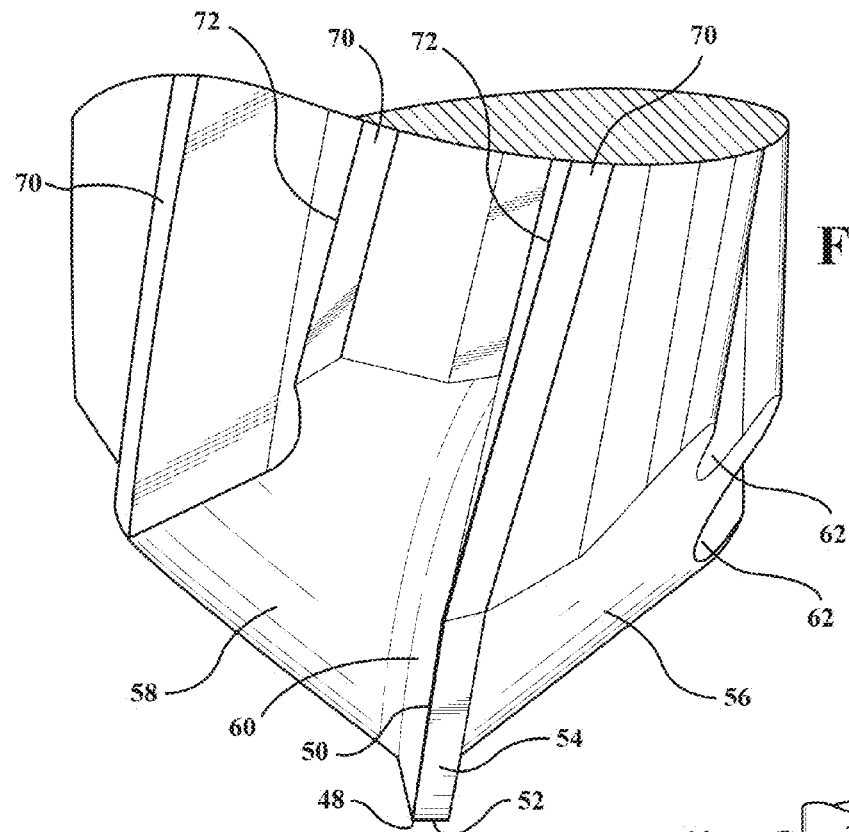
FIG. 10 is an enlarged view of the apical end of a rotary osteotome according to one embodiment of this invention.

A generally planar second trailing flank 56 is formed adjacent and falls away from each first trailing flank 54 at a second angle that is smaller than the first angle. In an example where the first trailing flanks 54 are formed at 45° (relative to the axis A), the second trailing flanks 56 may be 40° or less. A generally planar relief pocket 58 is formed adjacent and falls away from each second trailing flank 56 at a third angle smaller than the second angle. In an example where the second trailing flanks 56 are formed at 40° (relative to the axis A), the relief pockets 58 (i.e., the third angle) may be 30° or less. Each relief pocket 58 is disposed in a sector of the apical end 48 between a second trailing flank 56 and a lip 50. A generally axially disposed lip face 60 extends between the relief pocket 58 and the adjacent lip 50. This is perhaps best shown in the enlarged view of FIG. 10. When the osteotome 36 is rotated in the cutting direction, a significant amount of bone chips collect in the relief pocket 58 region. When the osteotome 36 is rotated in the burnishing direction, little to no bone chips collect in the relief pocket 58 region.

Figure 15A:
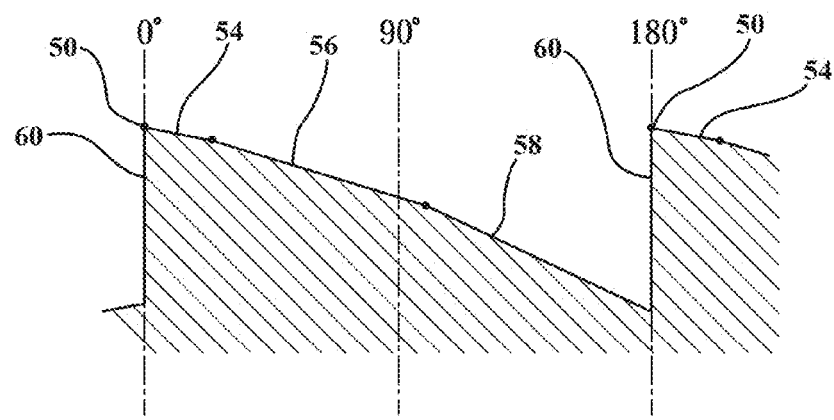
FIG. 15A is a cross-section of the apical end of an osteotome according to this invention taken generally along the semi-circular lines 15A-15A in FIG. 15.

FIG. 15A is a highly simplified and exemplary semi-circular cross-section through the apical end 48 of the osteotome 36, as taken along lines 15A-15A in FIG. 15. In this simplified illustration, small points are placed at the intersection of planar surfaces. The points do not exist in reality, but are merely added in this view to help distinguish boundaries of the different surfaces (54, 56, 58, 60). In combination with the several other views and descriptions, FIG. 15A will help inform the skilled artisan as to the various facets (54, 56, 58, 60) and their relationships to one another and to the lips 50.

A plurality of grooves or flutes 62 are disposed about the body 42. The flutes 62 are preferably, but not necessarily, equally circumferentially arranged about the body 42. The diameter of the body 42 may influence the number of flutes 62. As an example, bodies 42 in the range of about 1.5-2.8 mm may be formed with three or four flutes; bodies 42 in the range of about 2.5-3.8 mm may be formed with five or six flutes; bodies 42 in the range of about 3.5-4.8 mm may be formed with seven or eight flutes; and bodies 42 in the range of about 4.5-5.8 mm may be formed with nine or ten flutes. Of course, number of flutes 62 may be varied more or less than the examples given here in order to optimize performance and/or to better suit the particular application.

In the illustrated embodiment, the flutes 62 are formed with a helical twist. If the cutting direction is in the right-hand (clockwise) direction, then preferably the helical spiral is also in the right hand direction. This RHS-RHC configuration is shown throughout the Figures, although it should be appreciated that a reversal of cutting direction and helical spiral direction (i.e., to LHS-LHC) could be made if desired with substantially equal results. The diameter of the body 42 may influence the angle of the helical spiral. As an example, bodies 42 in the range of about 1.5-2.8 mm may be formed with a 9.5° spiral; bodies 42 in the range of about 2.5-3.8 mm may be formed with an 11° spiral; bodies 42 in the range of about 3.5-4.8 mm may be formed with a 12° spiral; and bodies 42 in the range of about 4.5-5.8 mm may be formed with a 12.5° spiral. Of course, the spiral angles may be varied more or less than the examples given here in order to optimize performance and/or to better suit the particular application.

Figure 16:
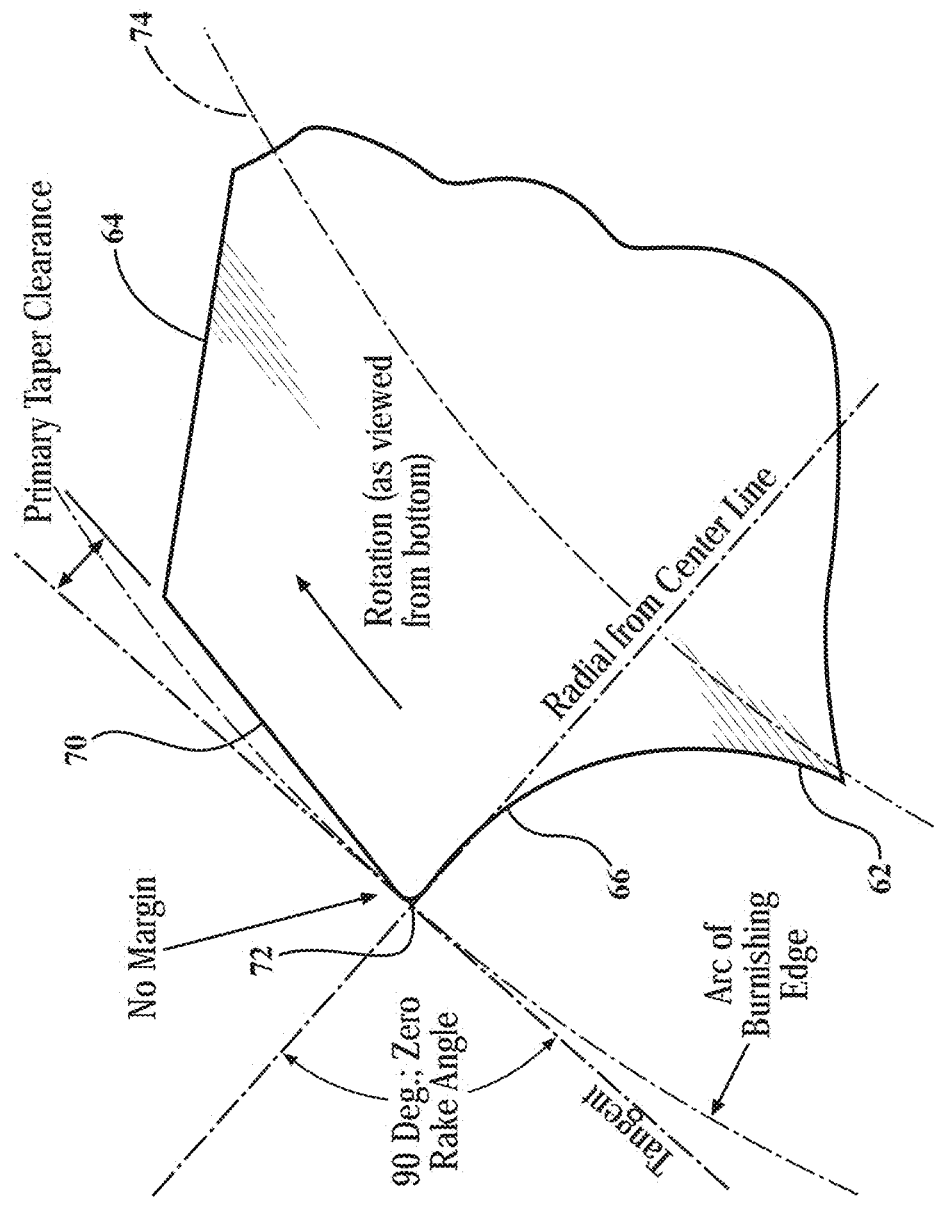
FIG. 16 is an enlarged view of a land as circumscribed at 16 in FIG. 15.

As perhaps best shown in FIGS. 15 and 16, each flute 62 has a burnishing face 64 and an opposing cutting face 66. A rib or land is formed between adjacent flutes 62, in alternating fashion. Thus, a four-flute 62 osteotome 36 will have four lands, a ten-flute 62 osteotome 36 will have ten interleaved lands, and so forth. Each land has an outer land face 70 that extends between the burnishing face 64 of the flute 62 on one side and the cutting face 66 of the flute 62 on its other side. The edge-like interface between each land face 70 and its associated cutting face 66 is referred to as a working edge 72. Depending on the rotational direction of the osteotome 36, the working edge 72 either functions to cut bone or burnish bone. That is, when the osteotome is rotated in the cutting direction, the working edges 72 slice and excavate bone (or other host material). When the osteotome is rotated in the burnishing direction, the working edges 72 compress and radially displace bone (or other host material) with little to no cutting whatsoever. This compression and radial displacement is exhibited as gentle pushing of the osseous structure laterally outwardly in a condensation mechanism. FIG. 15 depicts a web circle 74 superimposed as a broken circle. The web circle 74, or simply web 74, is the root or central portion of the body 42 that joins all of the lands. The diameter of the web circle 74 varies with the tapering diameter of the body 42.

In the preferred embodiment, the working edges 72 are substantially margin-less, in that the entire portion of each land face 70 is cut away behind the working edge 72 to provide complete clearance. In standard prior art burs and drills, margins are commonly incorporated behind the working edge to guide the drill in the hole and maintain the drill diameter. Primary taper clearance angles, i.e., the angle between a tangent of the working edge 72 and each land face 70 as shown in FIG. 16, may fall anywhere between about 1° and 30° depending upon the application. More preferably primary taper clearance angles will range between about 5°-20°. The diameter of the body 42 may influence the angle of the primary taper clearance. As an example, bodies 42 in the range of about 1.5-2.8 mm may have land faces 70 formed with a 15° primary taper clearance; bodies 42 in the range of about 2.5-3.8 mm may have land faces 70 formed with an 15° primary taper clearance; bodies 42 in the range of about 3.5-4.8 mm may have land faces 70 formed with a 12° primary taper clearance; and bodies 42 in the range of about 4.5-5.8 mm may have land faces 70 formed with a 10° primary taper clearance. Of course, the primary taper clearance angles may be varied more or less than the examples given here in order to optimize performance and/or to better suit the particular application. As mentioned above in connection with the angle of the helical twist, the substantially marginless working edges 72 are shown, for example in FIG. 14, turning away from the burnishing direction as the conically tapered profile of the body 42 decreases in diameter. In other words, when the burnishing direction is counter-clockwise as shown in FIG. 14, the helical twist of the working edges 72 winds in the counter-clockwise direction when viewed from the top of the body 42 looking toward its apical end 48. Or conversely, as shown in FIG. 14 when viewed from the apical end 48 looking toward top of the body 42, the twist will appear to be in the clockwise direction. Thus, when the burnishing direction is counter-clockwise, the working edges 72 will "turn away from the burnishing direction" when all of the land faces 70 and flutes 62 orbit counter-clockwise about the longitudinal axis A as one traces each land face 70 and flute 62 downwardly toward the apical end 48.

The cutting face 66 establishes a rake angle for each respective working edge 72. A rake is an angle of slope measured from the leading face of the tool (the working edge 72 in this case) to an imaginary line extending perpendicular to the surface of the worked object (e.g., inner bone surface of the osteotomy). Rake angle is a parameter used in various cutting and machining processes, describing the angle of the cutting face relative to the work. Rake angles can be: positive, negative or zero. The rake angle for working edge 72 when rotated in a cutting direction is preferably zero degrees (0°). In other words, the cutting face 66 is oriented approximately perpendicular to a tangent of the arc scribed through the working edge 72. As shown in FIG. 16, this establishes a crisp cutting edge 72 well-suited to cut/slice bone when the osteotome 36 is rotated in the cutting direction.

However, when the osteotome 36 is rotated in the burnishing direction, the rake angle is established between the working edge 72 and the land face 70, which as previously stated by lie at a large negative rake angle in the order of 10°-15° (for example). The large negative rake angle of the working edge 72 (when rotated in a burnishing direction) applies outward pressure at the point of contact between the wall of the osteotomy 32 and the working edge 72 to create a compression wave ahead of the point of contact, loosely akin to spreading butter on toast. Downward pressure applied by the surgeon is needed to keep the working edge 72 in contact with the bone surface of the osteotomy being expanded, that is, to keep it pushing on the compression wave. This is aided by the taper effect of the osteotomy and tool 36 to create lateral pressure (i.e., in the intended direction of expansion). The harder the surgeon pushes down, the more pressure is exerted laterally. This gives the surgeon complete control of the expansion rate irrespective to a large degree on the rotation speed of the osteotome 36. Thus, the burnishing effect's intensity depends on the amount of force exerted on the osteotome 36. The more force exerted, the quicker expansion will occur.

Figure 7:
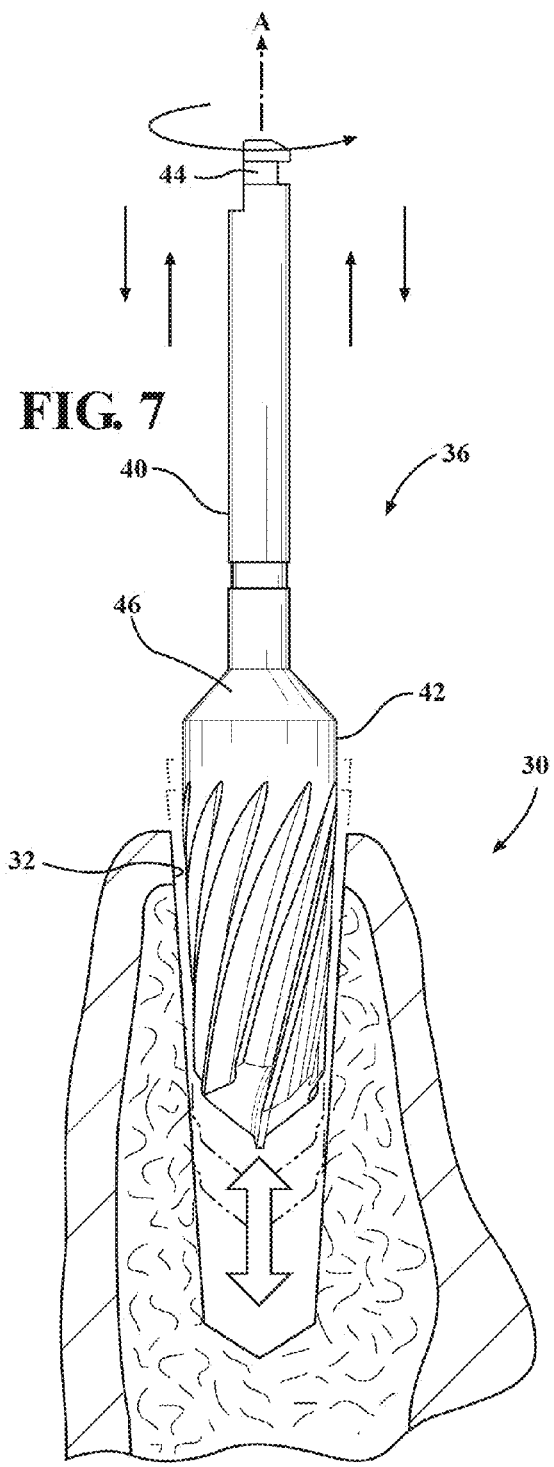
FIG. 7 is a simplified cross-sectional view showing a surgical procedure referred to herein as "bounce" where an osteotome according to the present invention is repeatedly pushed into the osteotomy and withdrawn while the osteotome remains spinning in a repetitive manner so as to enlarge the osteotomy while enabling the surgeon to manage the expansion rate (and other factors) while making adjustments on-the-fly.

As the working edge 72 drags across the bone, the force on the working edge 72 can be decomposed into two component forces: one normal to the bone's surface, pressing it outwardly, and the other tangential, dragging it along the inner surface of the osteotomy. As the tangential component is increased, the working edge 72 will start to slide along the bone. At the same time, the normal force will deform the softer bone material. If the normal force is low, the working edge 72 will rub against the bone but not permanently alter its surface. The rubbing action will create friction and heat, but this can be controlled by the surgeon by altering, on-the-fly, the rotation speed and/or pressure and/or irrigation flow. Because the body 42 of the osteotome 36 is tapered, the surgeon may at any instant during the surgical procedure lift the working edges 72 away from contact with the surface of the bone to allow air cooling and/or irrigation. This can be done in a controlled "bouncing" fashion where pressure is applied in short bursts with the surgeon continuously monitoring progress and making fine corrections and adjustments. See FIGS. 7 and 8 which illustrate this variable application of force and the ability for the osteotome to be lifted out of engagement—at any time during a procedure—with the walls of the osteotomy 32. As the surgeon-applied downward force increases, eventually the stresses in the bone's surface exceed its yield strength. When this happens, the working edge 72 will plow through the surface and create a trough behind it. The plowing action of the working edge 72 thus progressively enlarges the osteotomy.

Figure 9:
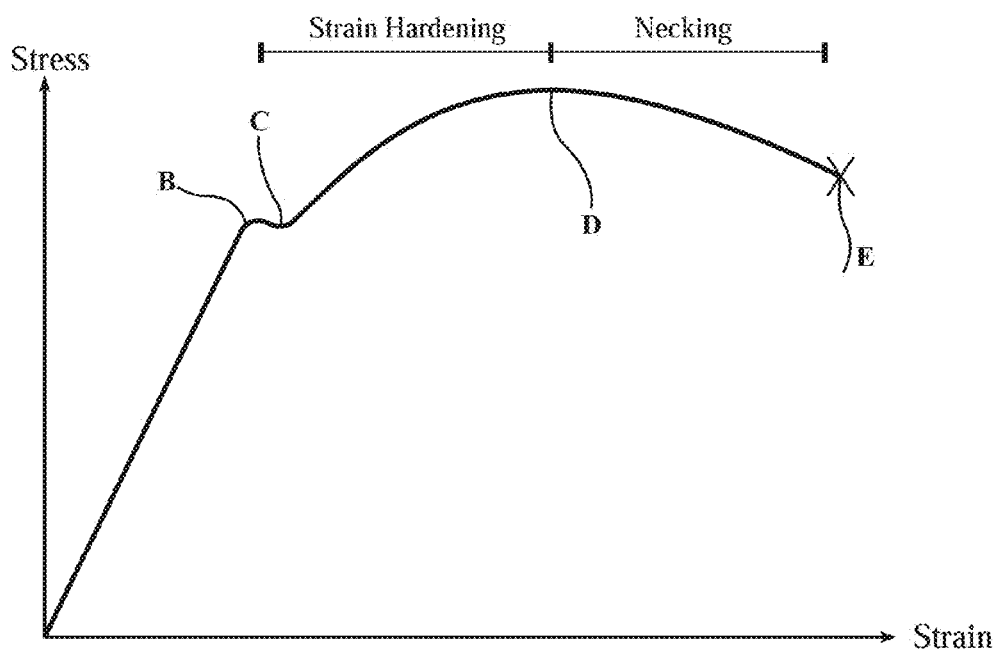
FIG. 9 is a simplified stress-strain curve generally representative of bone, metal foam and other host materials for with the present invention is suited for use.

FIG. 9 depicts a Stress-Strain curve that is generally illustrative for bone and other ductile materials including but not limited to foam metals of the type used in various commercial, industrial and aerospace applications. The straight-line segment of the curve from the point of origin (0,0) to B represents the material's elastic response region. Reference point B indicates the elastic limit of the material. While the elastic properties of bone are well-known, if the load imposed by the surgeon does not exceed the bone's ability to deform elastically, i.e., beyond point B, the bone will promptly return to its initial (un-deformed) condition once the stress is removed. On the other hand, if the load imposed by the surgeon exceeds the bone's ability to deform elastically, the bone will deform and change shape permanently by plastic deformation. In bone, the permanent change in shape is believed to be associated with micro-cracks that allow energy release, a compromise that is a natural defense against complete fracture. If these micro-cracks are small, the bone remains in one piece while the osteotomy expands. The region of plastic deformation extends from the yield point of the material (C), all the way to the point of fracture (E). The peak (D) of the curve between yield point (C) and fracture (E) indicates the material's ultimate tensile strength. When a material (e.g., bone or foam metal) is subjected to stress in the region between its yield point (C) and its ultimate tensile strength (D), the material experiences strain hardening. Strain hardening, also known as work hardening or cold working, is the strengthening of a ductile material by plastic deformation. This strengthening occurs because of dislocation movements and dislocation generation within the crystal structure of the material—which for bone materials corresponds with the above-mentioned micro-cracks. The material tends to experience necking when subjected to stress in the region between its ultimate tensile strength (D) and the point of fracture (E).

Figure 11:
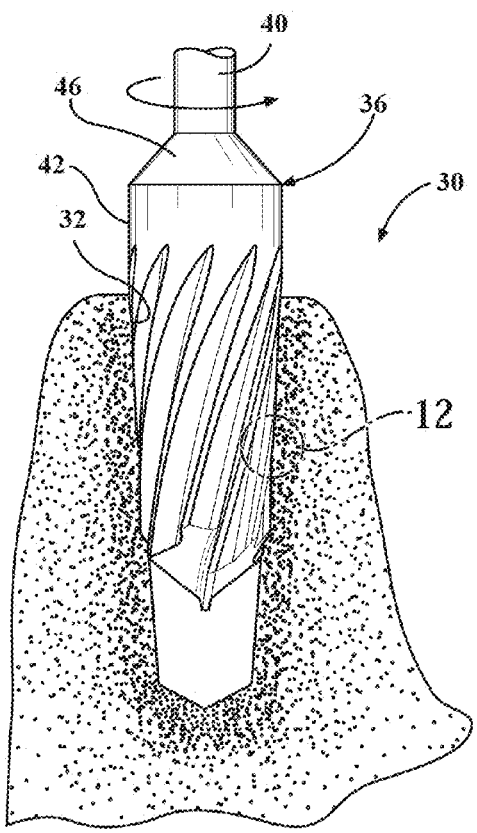
FIG. 11 depicts a cross-section through an osteotomy with a rotary osteotome disposed partially within as in the midst of an expansion procedure according to this invention.
Figure 20:
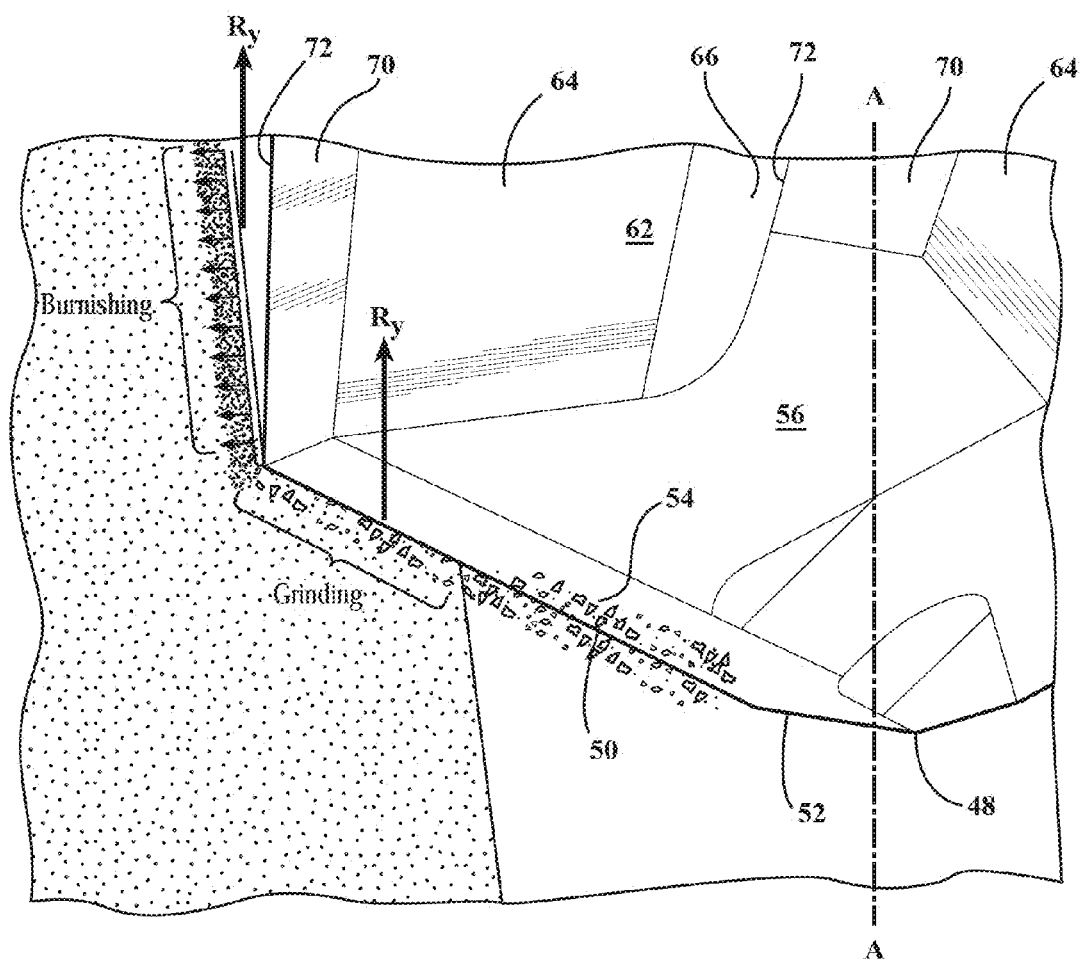
FIG. 20 is an enlarged view of the area circumscribed at 20 in FIG. 17 and depicting the bone grinding and auto-grafting features of the apical end.

The direction of helical twist can be designed so as to play a role in contributing to the surgeon's control so that an optimum level of stress can be applied to the bone (or other host material) throughout the expansion procedure. In particular, the RHS-RHC configuration described above, which represents a right-hand spiral for a right-hand cutting direction (or alternatively an LHS-LHC configuration, not shown) applies a beneficial opposing axial reaction force ($R_y$) when the osteotome 36 is continuously rotated at high speed in a burnishing direction and concurrently forcibly advanced (manually by the surgeon) into an osteotomy 32. This opposing axial reaction force ($R_y$) is illustrated graphically in FIGS. 11-13 as being directionally opposite to the forcibly advanced direction into the osteotomy 32. In other words, if the surgeon operating the osteotome 36 is pushing the osteotome 36 downwardly into an osteotomy 32, then the opposing axial reaction force ($R_y$) works in the opposite direction to push the osteotome upwardly. The opposing axial reaction force ($R_y$) is the vertical (or perhaps more accurately the "axial" vis-à-vis the longitudinal axis A) component of the reaction force (R) that is the Newtonian "equal and opposite reaction force" applied by the bone against the full length of the working edges 72 of the osteotome 36 (i.e., Newton's Third Law of Motion). An opposing axial reaction force ($R_y$) is also created by the effective a large negative rake angle at the lips 50 when the osteotome 36 is rotated in a burnishing direction, as shown in FIG. 20 and easily perceived from FIG. 15A. Those of skill in the art will appreciate alternative embodiments in which the opposing axial reaction force ($R_y$) is created by either the configuration of the lips 50 alone or of the working edges 72 alone rather than by both (50, 72) acting in concert as in the preferred embodiment.

In order for a surgeon to advance the apical end 48 toward the bottom of the osteotomy 32 when the osteotome 36 is spinning in the burnishing direction, he or she must push against and overcome the opposing axial reaction forces ($R_y$) in addition to supplying the force needed to plastically displace/expand the bone as described above. The osteotome 36 is designed so that the surgeon must continually work, as it were, against the opposing axial reaction forces ($R_y$) to expand an osteotomy by burnishing. Rather than being a detriment, the opposing axial reaction forces ($R_y$) are a benefit to the surgeon by giving them greater control over the expansion process. Because of the opposing axial reaction forces ($R_y$), the osteotome 36 will not be pulled deeper into the osteotomy 32 as might occur with a standard "up cutting" twist drill or burr that is designed to generate a tractive force that tends to advance the osteotome towards the interior of the osseous site; such up-cutting burrs have the potential to grab and pull the burr more deeply into the osteotomy, such that a surgeon could unexpectedly find themselves pulling up on a spinning burr to prevent over-penetration.

The intensity of the opposing axial reaction forces ($R_y$) is always proportional to the intensity of force applied by the surgeon in advancing the body 42 into the osteotomy 32. This opposing force thus creates real-time haptic feedback that is intuitive and natural to inform the surgeon whether more or less applied force is needed at any given instant. This concurrent tactile feedback takes full advantage of the surgeon's delicate sense of touch by applying reaction forces (R, and in particular the axial component $R_y$) directly through the osteotome 36. The mechanical stimulation of the opposing axial reaction forces ($R_y$) assists the surgeon to better control the expansion procedure on the basis of how the bone (or other host material) is reacting to the expansion procedure in real time.

Thus, the controlled "bouncing" described above in connection with FIGS. 7-9 is made more effective and substantially more controllable by the opposing axial reaction forces ($R_y$) so that the surgeon can instinctively monitor progress and make fine corrections and applied pressure adjustments on-the-fly without losing control over the rate of expansion. The tactile feedback from the opposing axial reaction forces ($R_y$) allows a surgeon to intuitively exert stress on the bone material so that its strain response preferably resides in the strain hardening zone, that is, between its yield point (C) to its ultimate tensile strength (D). In any event, the surgeon will endeavor to maintain the stress (as generated by the force he or she applies through the rotating osteotome 36) above the elastic limit (B) and below the point of fracture (E). Of course, until passing the applied stress passes the elastic limit (B), the bone will not permanently deform at all; and to apply stress beyond the point of fracture (E) will cause the bone (or other host material) to break—possibly catastrophically.

Figure 8:
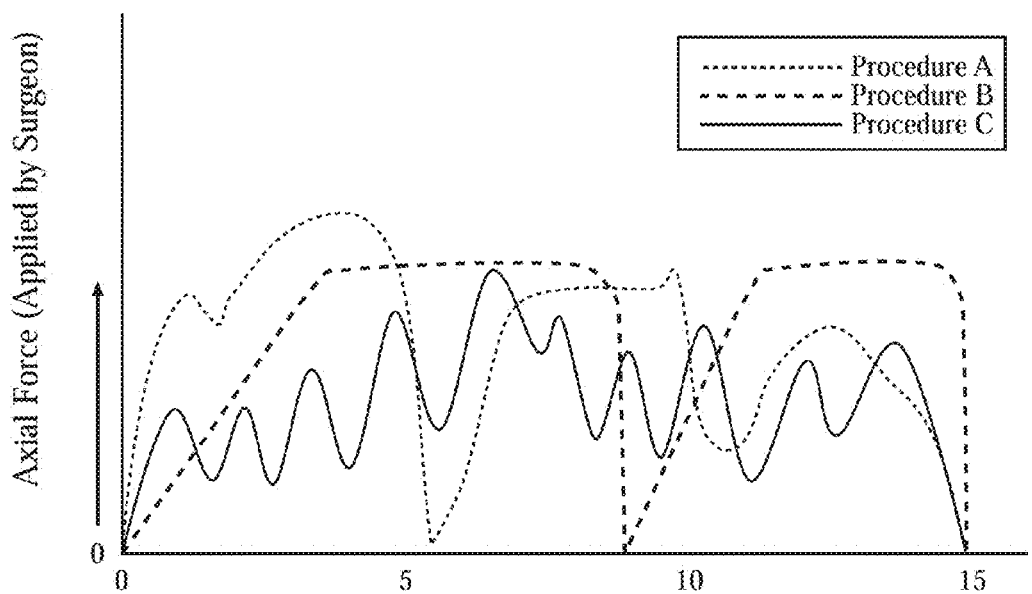
FIG. 8 is an exemplary graph plotting the force applied by a user to advance the body into an osteotomy against the depth of penetration into the osteotomy (or hole) in three separate procedures in order to illustrate that the surgeon (or user) can make on-the-fly adjustments to the advancing force depending on particular situation.

The exemplary graph in FIG. 8 plots the force applied by a surgeon to advance the body 42 into an osteotomy 32 against its depth of penetration into the osteotomy 32 in three separate procedures (A-B-C) to graphically show how the surgeon can make these on-the-fly adjustments depending on particular situation they encounter. The applied force is, as mentioned above, the force manually generated by the surgeon and needed to overcome the combined opposing axial reaction forces ($R_y$) plus the forces needed to expand/deform the bone. The applied force creates stress in the bone (or other host material), so that it develops a strain response like that shown in FIG. 9. During an operation, the surgeon uses his or her skill to manually vary the applied stress so that the strain response remains within the plastic deformation region (B-E), and more preferably still within the more ideal strain hardening region (C-D). The configuration of the osteotome 36 in this embodiment, therefore, is designed to give a surgeon more control during an expansion (by burnishing) procedure by generating proportional, opposing axial reaction forces ($R_y$) when the osteotome 36 continuously rotated and concurrently forcibly advanced into an osteotomy 32.

Figure 17:
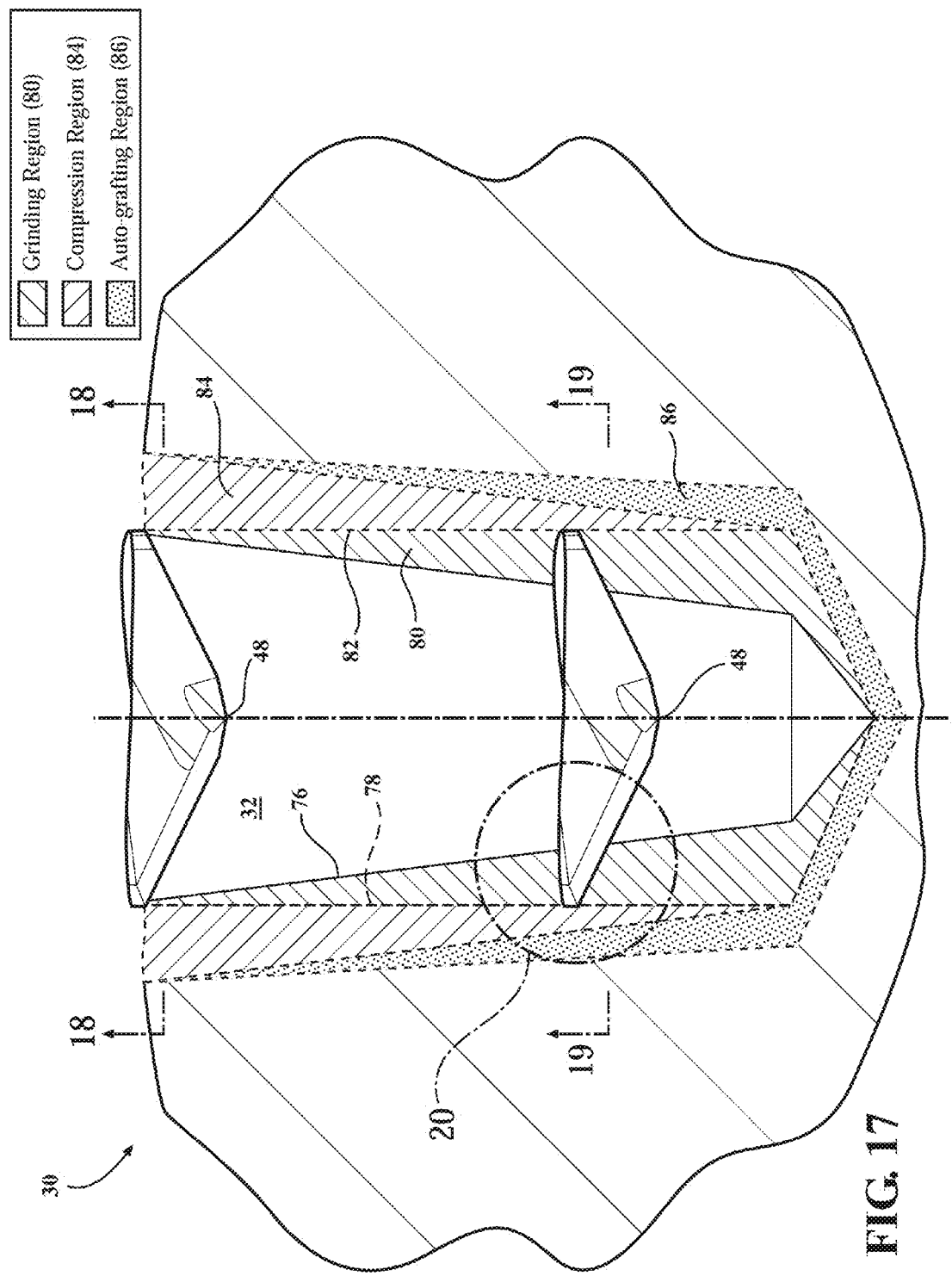
FIG. 17 is an exaggerated cross-section through an osteotomy with the apical end of a rotary osteotome shown at various stages of the expansion procedure in order to describe the zones of an osteotomy that experience grinding, compression and auto-grafting with each stage of the expansion process.
Figure 18:
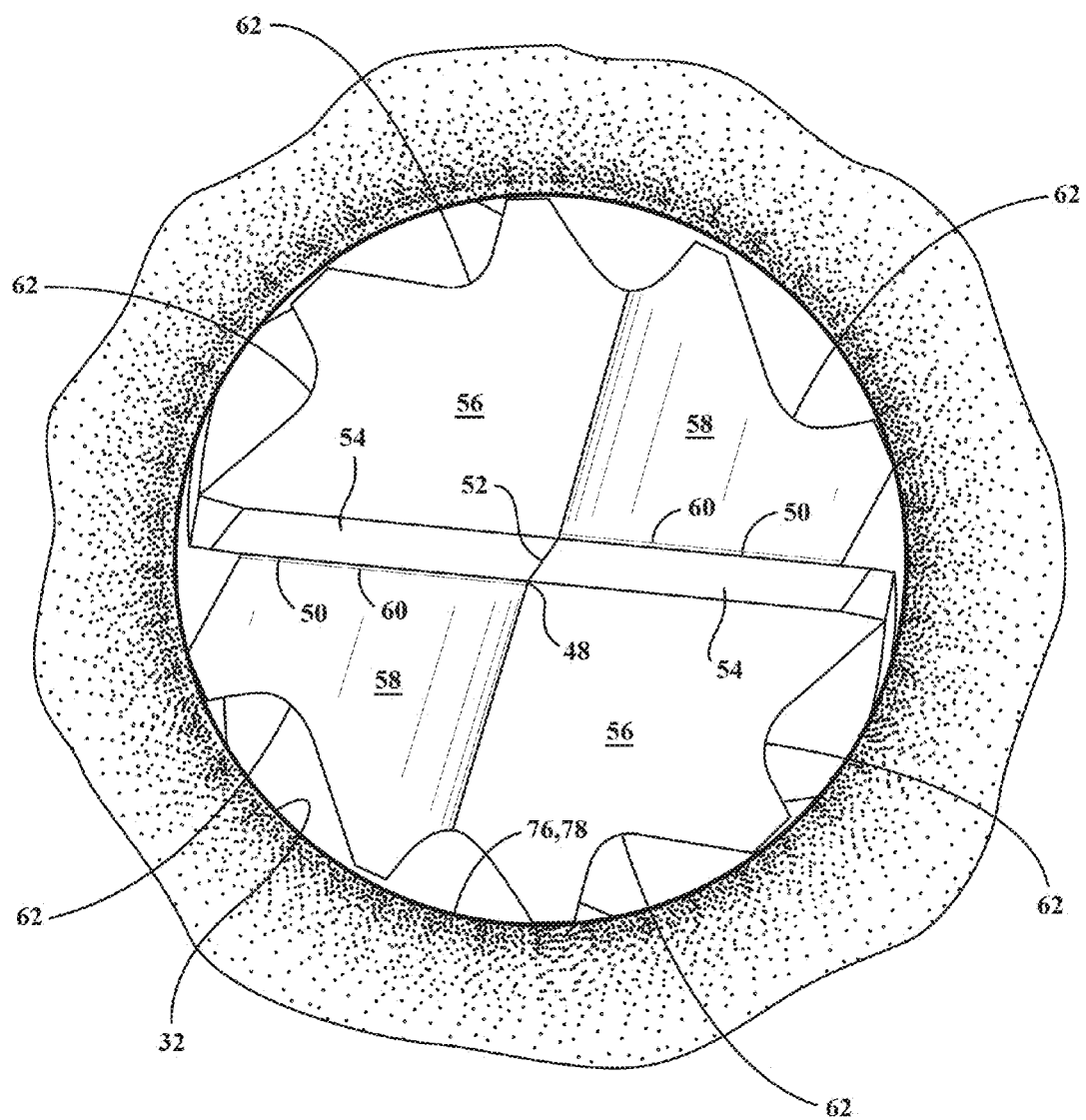
FIG. 18 is a cross-sectional view taken generally along lines 18-18 in FIG. 17.
Figure 19:
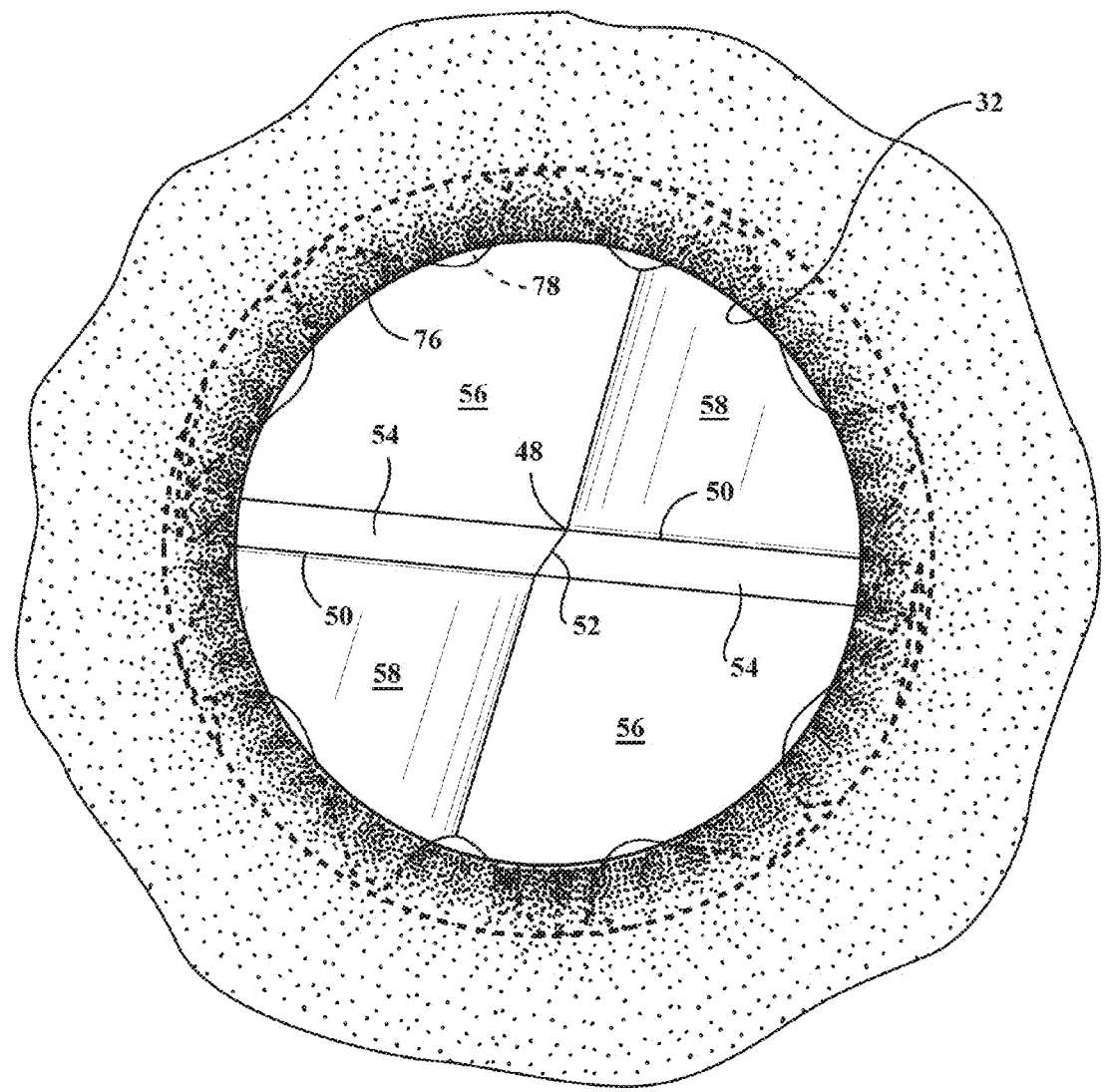
FIG. 19 is a cross-sectional view taken generally along lines 19-19 in FIG. 17.

Turning now to FIGS. 17-21, another novel aspect of the present invention is illustrated—namely the ability of the rotary osteotome 36 to simultaneously auto-graft and compact bone when the osteotome 36 is continuously rotated at high speed in a burnishing direction and concurrently forcibly advanced into an osteotomy 32. The compaction aspect may be defined as the gentle push of osseous structure laterally outwardly so as to condense the cells throughout the region surrounding the osteotomy 32. In FIG. 17, an osteotomy 32 formed by the present invention is shown with exaggerated taper on the order of ~7° (as compared with the preferred taper angle in the range of about 2°-3°) in order to highlight the necessary grinding of a small amount of bone (or other host material) with each progressively larger osteotome 36.

In FIG. 17, surface 76 indicates the inner wall of the osteotomy 32 as prepared in a preceding expansion operation by an osteotome 36 of smaller size. The apical end 48 of the next incrementally larger size osteotome 36 is shown in solid about to enter the osteotomy and again in phantom approximately ⅔ into the osteotomy 32. It is to be understood that the osteotome 36 is continuously rotated at high speed in a burnishing direction (e.g., counter-clockwise in the preceding examples) and concurrently forcibly advanced into an osteotomy 32 by the surgeon's manual efforts. Construction line 78 indicates the cylindrical (i.e., non-tapering) path of the apical end 48 as it moves from top to bottom within the osteotomy 32. In other words, the diameter of the apical end 48 remains the same, and therefore the diameter of its path also remains constant over the distance it travels. When the osteotome 36 first enters the osteotomy 32 as shown in solid, the internal diameter of the prior osteotomy 76 is approximately equal to the diameter of the apical end 48. However the internal diameter of the prior osteotomy 76 progressively narrows (i.e., tapers inwardly) toward the bottom of the osteotomy. Yet as shown the cylindrical path of the apical end 48 remains constant. Therefore, as the osteotome 36 is advanced deeper toward the bottom of the osteotomy 32, more and more bone is ground away and/or displaced to make room for the advancing (larger) osteotome 36. Region 80, defined as the annular space between surfaces 76 and 78 (plus a portion of the apical end 48), represents the bone material that is milled by the outermost edges of the lips 50 as the apical end 48 makes its way to the full depth of the osteotomy 32. The milled or ground region 80 includes not only the side walls, but also the bottom end of the osteotom 32. In a subsequent operation (not shown), when another osteotome 36 of the next larger size is used to further expand the osteotomy 32, a similar (but larger) region 80 will exist as its apical end is pushed to the bottom of the osteotomy 32, and so on.

Remaining within the context of FIG. 17, surface 82 indicates the outer wall of the osteotomy 32 as prepared by the expansion operation of osteotome 36 whose apical end 48 is illustrated in solid and phantom. The surface 82 is a substantially perfect negative of the revolving osteotome body 42. In other words, the surface 82 will have a taper equal to that of the osteotome body 42, and a bottom impression made by the spinning apical end 48 of the osteotome illustrated. Region 84, defined as the annular space between surfaces 78 and 82, represents the bone material that is plastically displaced by the working edges 72 of the lands as the osteotome body 42 makes its way to the full depth of the osteotomy 32. All of the bone material within region 84 is compressed radially outwardly into the surrounding bone structure without cutting, and therefore represents a zone of densified bone.

An important observation may be stated as: "What happens to the ground/milled bone material that once occupied region 80?". As alluded to previously, the osteotome 36 is configured to simultaneously auto-graft and compact the ground/milled bone from region 80 as it is rotated and forcibly advanced into the osteotomy 32. The auto-grafting phenomena supplements the basic bone compression and condensation effects described above to further densify the inner walls 82 of the osteotomy. Furthermore, auto-grafting—which is the process of repatriating the patient's own bone material—enhances natural healing properties in the human body to accelerate recovery and improve osseointegration.

Figure 21:
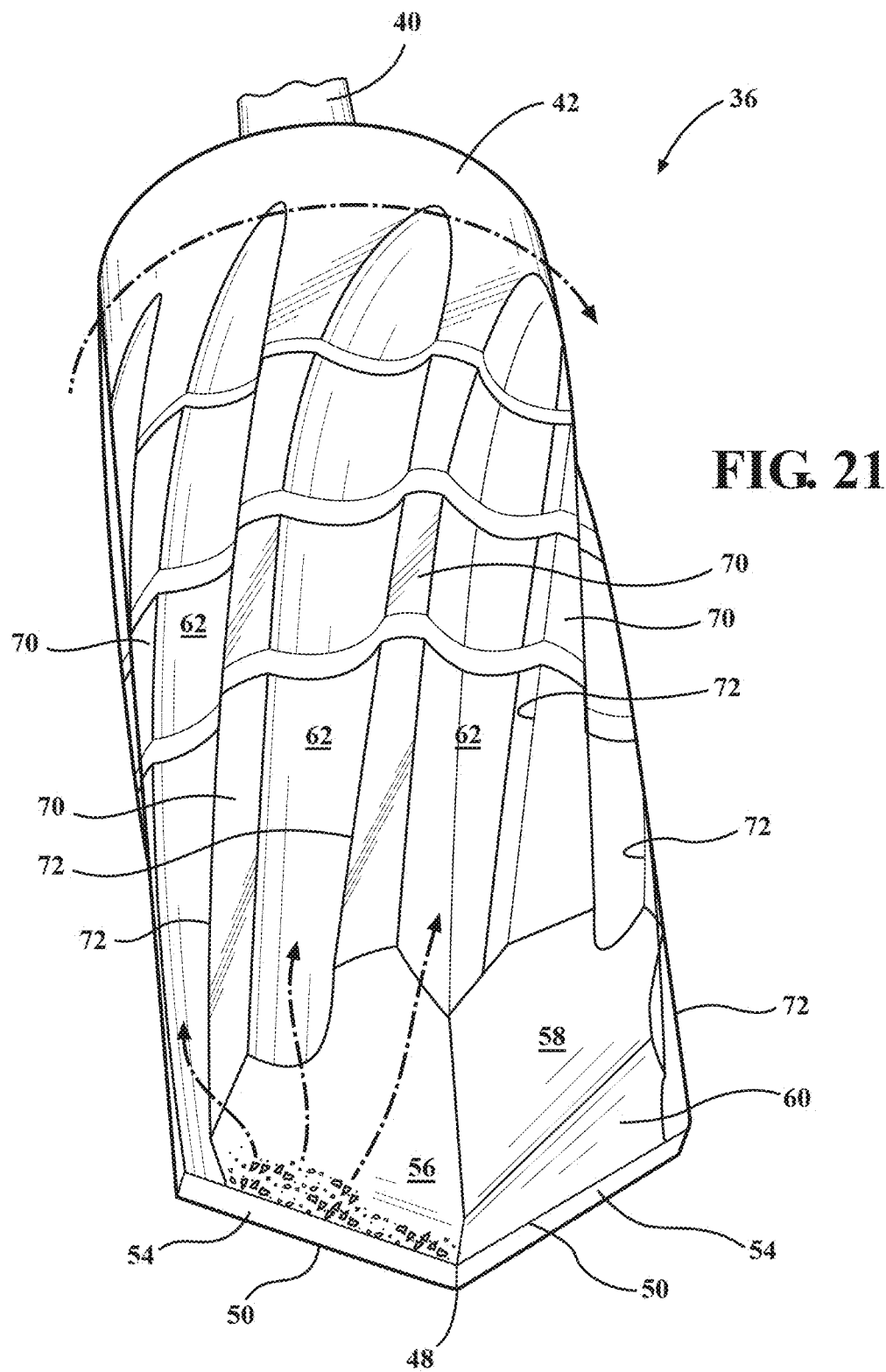
FIG. 21 is a fragmentary perspective view of the apical end as in FIG. 14 but from a slightly different perspective and illustrating the region of the apical end where bone material collects and is subsequently repatriated into surrounding bone.

Turning to FIG. 20, an enlarged view is shown of the interface between the apical end 48 and the host bone material. At the point where the outermost edge of each rotating and forcibly advancing lip 50 contacts the bone, attrition causes the bone to be ground away. The bone debris collects mainly on the second trailing flanks 56, i.e., immediately behind the respective first trailing flanks 54. Some of the accumulated bone debris migrates radially inwardly along the lips 50 and is carried all the way to the very bottom of the osteotomy 32. The remainder of the accumulated bone debris is distributed along the flutes 62 which directly intersect the second trailing flanks 56 by the pressure exerted through the surgeon's manual pushing efforts. This is illustrated in FIG. 21. It is possible that a small fraction of bone debris could spill over into the relief pockets 58, but this is of minimal significance. Bone debris that is distributed up the flutes 62 works its way toward the associated land faces 70 where it is wiped and pressed into the cellular walls of the osteotomy 32—i.e. where it is grafted back into the patient's bone very near to the sight were it was harvested. Bone debris that is carried to the bottom of the osteotomy 32 is wiped and pressed into the bottom of the osteotomy 32. As a result, an auto-grafting zone 86 is developed around and under the compaction region 84, as shown in FIG. 17. Interestingly, the auto-grafting zone 86 is thinnest where the compaction zone 84 is thickest, and conversely the auto-grafting zone 86 is thickest where the compaction zone 84 is thinnest. And at the osteotomy bottom where this is little-to-no compaction at all, there is a significant zone of auto-grafting 86 which serves to densify (and positively stimulate) an area of the osteotomy 32 which could otherwise not be densified. It can therefore be appreciated that the auto-grafting phenomena is an ideal complement to the basic bone compression and condensation effects in preparing an osteotomy 32 to receive an implant 34 or other fixation device.

To summarize, the present invention describes a method for enlarging an osteotomy 32 by burnishing (and/or by cutting when rotation is reversed). The basic steps of the method include: supporting a fluted body 42 for rotation about a longitudinal axis A, the body 42 having an apical end 48 and a conically tapered profile decreasing from a maximum diameter to a minimum diameter adjacent the apical end 48. The body 48 is continuously rotated in a burnishing direction while concurrently forcibly advancing the body 42 (by the manual efforts of the surgeon) into an osteotomy 32. Notable improvements include: grinding a progressively larger amount of bone material with the apical end 48 as the body 42 is advanced deeper into the osteotomy 32, auto-grafting the ground bone material into the host bone within the osteotomy 32 and compacting the ground bone material into the host bone with the fluted body 42, and also generating an opposing axial reaction force ($R_y$) in opposition to the advancing direction of the body 42 into the osteotomy 32. The opposing axial reaction force ($R_y$) is created by the configuration of the lips 50 and/or the working edges 72.

The tools and techniques of this invention are readily adaptable to the methods of computer generated implant placement guides, like those described for example in U.S. Pat. No. 6,814,575 to Poirier, issued Nov. 9, 2004 (the entire disclosure of which is hereby incorporated by reference). According to these methods, a computer model is created giving jawbone 30 structural details, gum surface shape information and proposed teeth or dental prosthesis shape information. The computer model shows the bone structure, gum surface and teeth images properly referenced to one another so that osteotomy 32 positions can be selected taking into consideration proper positioning within the bone 30 as well as proper positioning with respect to the implant 34.

These and other benefits will be appreciated by the following details of exemplary test details describing a mechanical validation of bone burnishing induced by the osteotome 36 and method described above for the surgical preparation and expansion of an implant site in bone.

Example

The mechanical tests were conducted with a surgical drill motor 38 and materials testing machine to control the rotary speed and depth penetration rate while measuring force and torque during drilling/burnishing procedures in bone. In other words, the manual influence of a surgeon was not involved in the following test report. The procedures using a prior art burr drill, fluted osteotome 36 in "Burnishing Mode" (Burnishing Osteotome), and fluted osteotome 36 in "Drilling Mode" (Osteotome Drill) were compared for insertion and removal torque of a 3.8 mm or 6.0 mm implant 34. Heat generation was measured during the drilling procedure by inserting a thermocouple into the bone, 1 mm away from the edge of the hole. Procedures included, drilling (900 RPM) without irrigation and burnishing (200, 400, 600, 900, and 1100 RPM), with and without irrigation. The implant 34 stability was also measured with the Osstell resonance frequency analysis system. The morphology of bone around the holes was imaged with optical microscopy and with an environmental scanning electron microscopy (ESEM) and the bone mineral density (BMD) and bone volume fraction (BVF) were quantified with micro-computed tomography (μCT) imaging. The final diameter of the prepared osteotomy was measured at two depth levels, one cm apart.

A detailed Standard Operating Procedure (SOP) was developed and followed during all mechanical tests. Briefly, three porcine tibial plateau bone samples with the articular surfaces and subchondral bone (approximately 5-10 cm thickness) removed were mounted in epoxy potting and a custom clamping system. The clamp was in turn fixed to an ElectroPlus E10000 materials testing system by way of a biaxial load cell for measurement of the applied force and torque during the drilling/osteotomy procedures. A surgical drilling mechanism 38 with controllable motor speed and a torque limiter (3i Implant Innovations, WS-75) was mounted to the crosshead of the materials testing system.

The testing system was programmed for displacement control with a constant linear rate into and back out at progressive depths until the target depth of the burr/osteotome of 13 mm was achieved. Five diameter steps were used to progressively enlarge the hole. Prior art surgical drilling burrs with maximum diameters of 1.8, 2.8, 3.8, 4.8, and 5.2 mm were used, while the Fluted Osteotomes had maximum diameters of 1.8, 2.8, 3.8, 4.8 and 5.8 mm. After these enlargement steps were completed, a 6.0 mm diameter implant was inserted into seven of the holes. In three cases a 3.8 mm diameter implant was inserted into the holes after the 3.8 mm step was completed, and after removal of the 3.8 mm implant the progressive hole enlargement continued.

Heat generation was measured during the testing procedures by inserting a thermocouple into the bone, approximately one mm away from the edge of the hole. The maximum temperatures were recorded during the drilling/burnishing procedures in six of the tests.

After the procedure was completed, an implant was inserted into the hole while measuring the force and torque required for insertion. The implant stability was measured with resonance frequency analysis (RFA) with the Osstell measurement device.

Additional implant holes were created with similar procedures, but with no insertion of an implant 34. A total of 14 tests were completed with three holes (anterior, central, and posterior) aligned in rows on the medial and lateral sides of the proximal tibias with a minimum spacing of 6 mm between holes.

Imaging and characterization of the compacted bone was conducted using microcomputed tomography ($\mu$-CT). High resolution CT slices were aligned along the axis of the holes at a voxel resolution of 90 $\mu$m. Regions of interest were selected and the bone mineral density, and bone volume fraction was quantified as a function of distance from the edge of the hole and depth using GE Microview software.

Imaging and characterization of the compacted bone was conducted using an optical and an ESEM. The bone samples were sectioned along the center axis of the implant hole for microscopy imaging. Low-magnification images of the radial edges of the osteotomy was taken at 20×-50× magnification with an optical microscope.

The Fluted Osteotome burnishing technique was shown to increase the required penetration force and torque compared with drilling (Table 1). Force and torque during burnishing were also correlated with the expansion step diameter, so that the highest values (73 N and 18.9 Ncm) occurred during the 5.8 mm step. The 3.8 mm diameter implant was inserted into drilled holes (the maximum torque was 15 and 20 Ncm) and in one burnished hole (the maximum value could not be recorded due to damage to the implant).

TABLE 1

MEASURED MAXIMUM PENETRATION FORCE AND TORQUE DURING THE FIVE DIAMETER EXPANSION STEPS.

| | | Maximum Force (N) | | | | | Maximum Torque (Ncm) | | | | |
|---|---|---|---|---|---|---|---|---|---|---|---|
| Test | Procedure | 1.8 mm | 2.8 mm | 3.8 mm | 4.8 mm | 5.2/5.8 mm | 1.8 mm | 2.8 mm | 3.8 mm | 4.8 mm | 5.2/5.8 mm |
| Porcine01_AntMed | Burr drilling | 12.5 | 13 | 3 | 6.5 | 8 | 2.5 | 2.5 | 2 | 2.5 | 4 |
| Porcine01_CentMed | Osteotome drilling | 13 | 7 | 14 | 11 | 10 | 2 | 3 | 3.5 | 5 | 6.5 |
| Porcine01_PostMed | Osteotome burnishing | 20 | 20.5 | 40 | 60 | 70 | 3 | 5 | 10 | 18 | 24 |
| Porcine02_CentMed | Osteotome burnishing | 10 | 10 | 60 | 50 | 24 | 1.5 | 1 | 4 | 8.5 | 28 |
| Porcine02_AntMed | Burr drilling | 9 | 9 | 10 | 11 | 3.5 | 1 | 1.5 | 1.5 | 3 | 2.5 |
| Porcine02_PostMed | Osteotome burnishing | | 7 | 27 | 70 | 100 | | 2.5 | 10 | 35 | 15 |
| Porcine02_AntLat | 200 RPM burnishing | 33 | 16 | 170 | 40 | 140 | 3.5 | 2.5 | 12 | 15 | 27 |
| Porcine02_CentLat | 400 RPM burnishing | 9 | 10 | 34 | 30 | 40 | 1 | 2.5 | 7 | 10 | 15.5 |
| Porcine02_PostLat | 1100 RPM burnishing | 11 | 11 | 38 | 20 | 27 | 1 | 1.5 | 5.5 | 6 | 9 |
| Porcine03_AntMed | Burr drilling | 10 | 13 | 3 | 11 | 14 | 1 | 1.5 | 1 | 2.5 | 3 |
| Porcine03_CentMed | Osteotome drilling | 9 | 4 | 3.5 | 5 | 5 | 1 | 1.5 | 2.5 | 3 | 4.5 |
| Porcine03_Post Med | Osteotome burnishing | 10 | 14 | 23 | 11 | 110 | 1.5 | 1.5 | 6 | 2.5 | 13.5 |
| Average | Drilling | 10.7 | 9.2 | 6.7 | 8.9 | 8.1 | 1.5 | 2 | 2.1 | 3.2 | 4.1 |
| | Burnishing | 15.5 | 12.6 | 56.0 | 40.1 | 73 | 1.9 | 2.4 | 7.8 | 13.6 | 18.9 |

For the 6.0 mm diameter implant, the insertion and removal torques in drilled holes were approximately 35 Ncm and 21 Ncm, respectively while burnishing greatly increased these torques to 80 Ncm and 60 Ncm, respectively (Table 2). Bone burnishing produced higher maximum temperatures than drilling when the irrigation was turned off. With irrigation turned on burnishing only increased the maximum temperature by approximately 10° F. There were no noticeable differences between temperature or implant insertion and removal torques with different burnishing speeds. There was a trend for reduced maximum penetration force and torque at higher burnishing speeds, such that at 1100 RPM the Maximum Force was only 27 N and the Maximum Torque was only 9 Ncm.

TABLE 2

MEASURED MAXIMUM TEMPERATURE, INSERTION AND REMOVAL TORQUES.

| Test | Procedure | Maximum temperature (° F.) | 3.8 mm implant insertion Torque (Ncm) | 6.0 mm implant insertion Torque (Ncm) | 6.0 mm implant removal Torque (Ncm) |
|---|---|---|---|---|---|
| Porcine01__AntMed | Burr drilling | | | 30 | 30 |
| Porcine02__CentMed | Osteotome burnishing | 150 (no irrigation) | | | |
| Porcine02__AntMed | Burr drilling | 83 (no irrigation) | | | |
| Porcine02__PostMed | Osteotome burnishing | 91 | | | |
| Porcine02__Antlat | 200 RPM burnishing | 73 | | 120 | 61 |
| Porcine02__CentLat | 400 RPM burnishing | 81 | | 76 | 45 |
| Porcine02__Postlat | 1100 RPM burnishing | 81 | | 65 | 46 |
| Porcine03__AntMed | Burr drilling | | 15 | 35 | 20 |
| Porcine03__CentMed | Osteotome drilling | | 20 | 35 | 22 |
| Porcine03__PostMed | Osteotome burnishing | | (stripped) | 70 | 89 |
| Average | Drilling | | | 35 | 21 |
| | Burnishing | | | 80 | 60 |

Osstell "Implant Stability Quotient" (ISQ) measurements were approximately 73 for the 3.8 mm implant diameter in the drilled holes, but no measurement could be made on the damaged implant in the burnished hole (Table 3). The 6.0 mm implant showed similar ISQ measurements of approximately 82 for both the drilled and burnished holes.

TABLE 3

ISQ MEASUREMENTS FOR VARIOUS ORIENTATIONS RELATIVE TO THE BONE.

| Test | Procedure | 3.8 mm Osstell (ISQ) Ant | Med | Post | Lat | 6.0 mm Osstell (ISQ) Ant | Med | Post | Lat |
|---|---|---|---|---|---|---|---|---|---|
| Porcine01__AntMed | Burr drilling | | | | | 81 | 80 | 81 | 80 |
| Porcine01__CentMed | Osteotome drilling | | | | | 85 | 82 | 85 | 82 |
| Porcine01__PostMed | Osteotome burnishing | | | | | 84 | 81 | 84 | 81 |
| Porcine01__CentCent | Summers Osteotome | | | | | 78 | 82 | 81 | 82 |
| Porcine03__AntMed | Burr drilling | 72 | 76 | 72 | 72 | 80 | 81 | 81 | 81 |
| Porcine03__CentMed | Osteotome drilling | 75 | 75 | 67 | 75 | 84 | 83 | 84 | 81 |
| Porcine03__Post Med | Osteotome burnishing | | | | | 82 | 80 | 82 | 80 |
| Average | Drilling | | 73 | | | | 82 | | |
| | Burnishing | | | | | | 82 | | |

There was not a noticeable difference in the diameter of holes created by the prior art burr drill or the present osteotome 36 (in either of its drilling/cutting or burnishing modes), however this may have been due to the insertion of the 6.0 mm implant into many of the holes prior to Micro-CT imaging. The osteotome 36 had a larger apex and top diameter (4.8 mm and 5.8 mm, respectively) compared with the prior art burr (4.2 mm and 5.2 mm, respectively). In the case of Porcine02 medial tibial plateau, no implant was inserted into the holes created with the burr drilling or fluted osteotome burnishing techniques before μCT imaging. The diameters of these holes are smaller than other holes and demonstrate that although the osteotome 36 has a larger diameter than the prior art burr, there is more elastic recovery after the osteotome 36 is removed and therefore ultimately creates a smaller diameter hole. Even the osteotome drilling/cutting procedure seemed to make a smaller diameter hole than the prior art burr, relative to the size of these two tools.

Micro-CT imaging revealed compaction of bone around the periphery of holes created with burnishing and relatively increased bone mineral density around these holes on the other hand imaging showed relative constant bone mineral density around holes created through drilling. For example, FIG. 22 is a micro-CT image showing a transverse slice through a Porcine03 medial tibial plateau with comparative holes created by: (A-left) a prior art burr drill, (B-center) the rotary osteotome 36 rotated in a drilling/cutting direction, and (C-right) the rotary osteotome 36 rotated in a burnishing direction. There was bone mineral density variation across the tibial plateau with the highest on the medial side, followed by the lateral side and lowest in the central region. None of the holes were created into regions of cortical bone, but one hole extended through the entire depth of the trabecular region and into the bone marrow cavity. Axial projection through a 1 cm volume of bone demonstrated a "halo" of compacted bone by averaging over the varying trabecular density. See for example FIGS. 23A-D which are micro-CT images that show comparative axial slice views of Porcine03 medial tibial plateau holes created with a prior art burr drill (FIG. 23A) and the rotary osteotome 36 rotated in a burnishing direction (FIG. 23C). Also shown are comparative axial slice views of average bone mineral density projection of 1 cm volume around Porcine02 medial holes created with a prior art burr drill (FIG. 23B) and the rotary osteotome 36 rotated in a burnishing direction (FIG. 23D).

TABLE 4

HOLE DIAMETER MEASUREMENTS AT LOCATIONS 1 CM APART.

| Test | Procedure | Empty Diameter (mm) | |
|---|---|---|---|
| | | Distal | Proximal |
| Porcine01__AntMed | Burr drilling | 4.9 | 5.7 |
| Porcine01__CentMed | Osteotome drilling | 4.4 | 5.5 |
| Porcine01__PostMed | Osteotome burnishing | 4.2 | 5.2 |
| Porcine02__CentMed | Osteotome burnishing | 4.6 | 5.3 |
| Porcine02__AntMed | Burr drilling | 4.4 | 5.6 |
| Porcine02__PostMed | Osteotome burnishing | 4.5 | 5.3 |
| Porcine02__AntLat | 200 RPM burnishing | 4.7 | 5.4 |
| Porcine02__CentLat | 400 RPM burnishing | 5.1 | 5.3 |
| Porcine02__PostLat | 1100 RPM burnishing | 4.6 | 5.5 |
| Porcine03__AntMed | Burr drilling | 4.7 | 5.7 |
| Porcine03__CentMed | Osteotome drilling | 4.7 | 5.9 |
| Porcine03__PostMed | Osteotome burnishing | 4.8 | 5.5 |
| Average | Burr Drilling | 4.7 | 5.7 |
| | Osteotome Drilling | 4.6 | 5.7 |
| | Osteotome Burnishing | 4.6 | 5.4 |

Scanning electron microscopic images showed relatively similar roughness on the surface of holes created by the prior art burr drill and the osteotome 36 when rotating in the cutting/drilling direction, while the burnishing osteotome technique produced a surface that looked considerably smoother. Bone burnishing resulted in a layer of granulated bone particles that were compacted onto the surface of the length of the osteotomy hole (i.e., auto-grafted) especially near the bottom surface of the holes.

The results of this mechanical validation study demonstrated that the burnishing method greatly increases the insertion and removal torques and creates a region of compacted bone particles and increased bone mineral density around the periphery of the hole. The bone burnishing technique produces elastic strain around the burnished holes. The burnishing technique follows a similar clinical procedure to the standard drilling technique. Although penetration forces and torques were increased, there were only limited increases in temperature around the hole when irrigation and a "bouncing" method (FIGS. 7 and 8) were used. Osstell did not indicate any differences between the ISQ of drilled versus burnished holes, but all readings were considered to be in the "stable" range. The lack of sensitivity of the Osstell measurements may be due to the inherent stability of the 6.0 mm diameter by 11 mm long implant.

Test results showed that the bone burnishing technique of this invention increases the bone mineral density around the periphery of the osteotome hole. The bone burnishing technique increases the implant primary stability by generating higher insertion and removal torques on the implant. The bone burnishing technique auto-grafts bone by reapplying ground particles in a compacted manner along the entire depth of the osteotome hole, particularly at the bottom of the hole. The bone burnishing technique has similar clinical safety to prior art burr drilling when proper rotary speed, penetration speed and irrigation are used. The bone burnishing technique creates a smaller hole than drilling due to recovery of elastic strain when the osteotome is removed from the hole.

Alternate Embodiments and Applications

Figure 24:
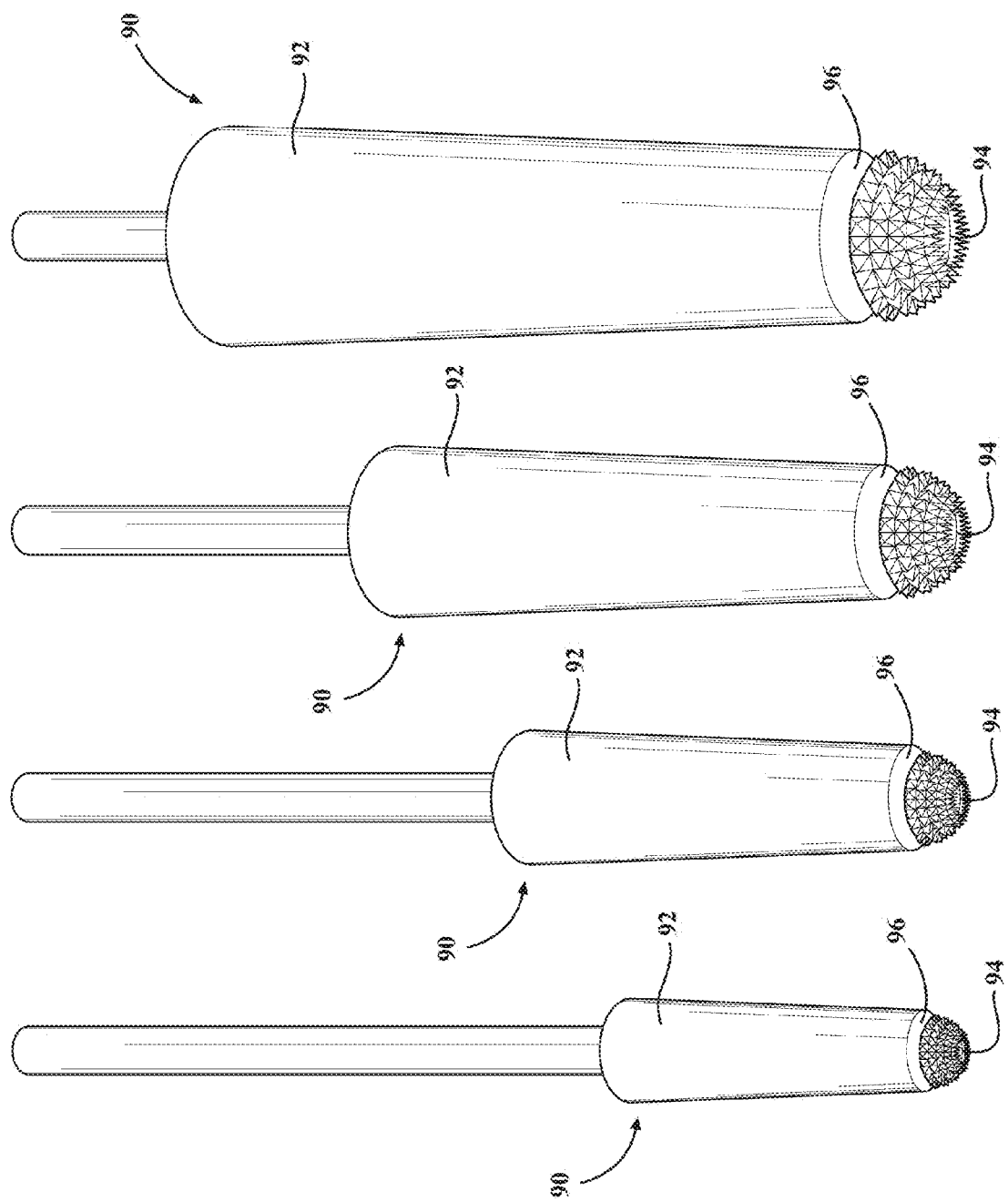
FIG. 24 shows an alternative embodiment of the osteotome of this invention configured for high-frequency vibration rather than rotation.
Figure 26:
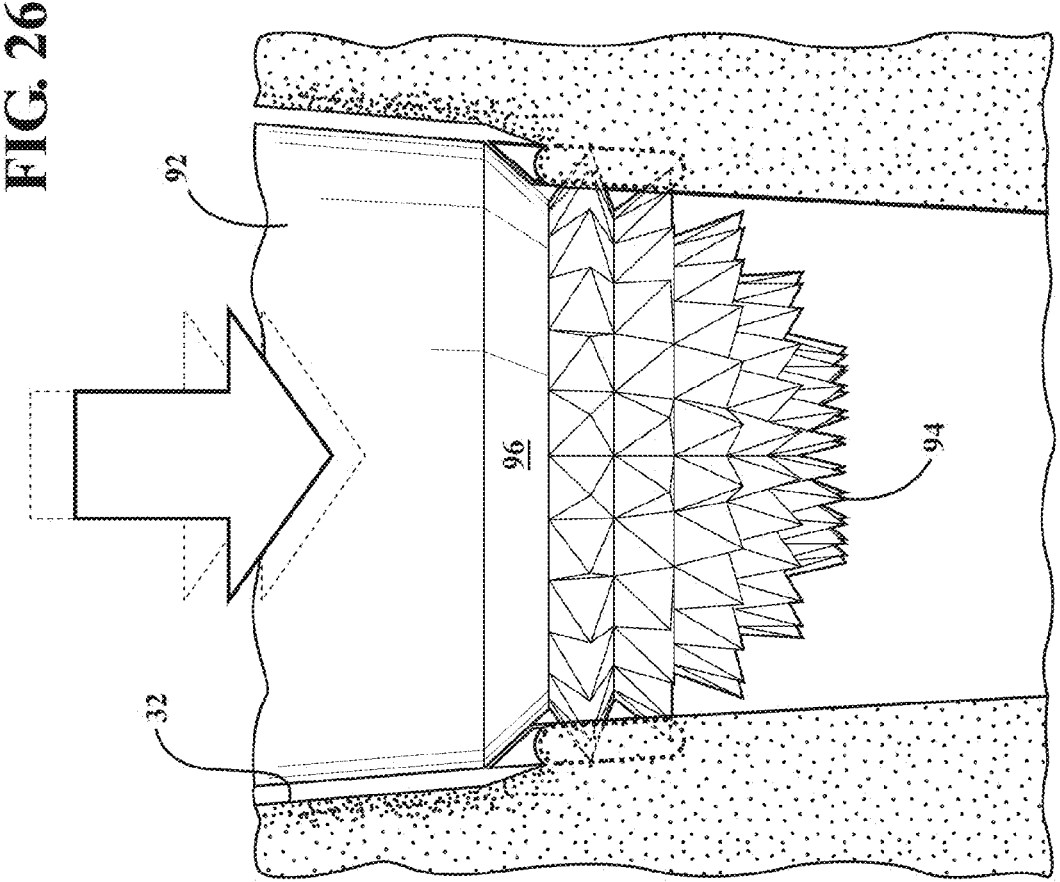
FIG. 26 is an enlarged view of the apical end of the alternative osteotome of FIG. 24.
Figure 25:
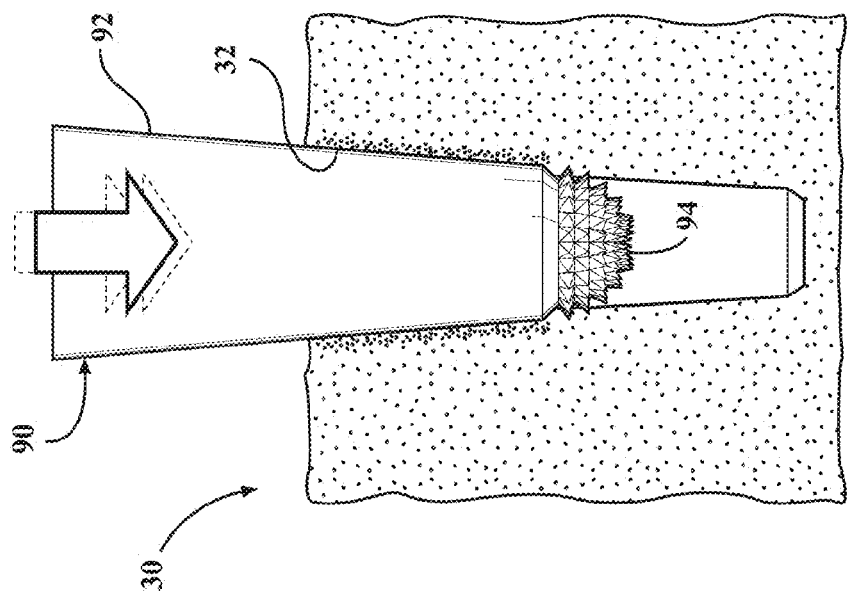
FIG. 25 is a cross-section through an osteotomy with the alternative osteotome of FIG. 24 disposed partially completing an expansion procedure according to this invention.

FIGS. 24-26 illustrate an alternative embodiment of this invention, namely an ultrasonic osteotome 90 configured to enlarge an osteotomy without rotation. The ultrasonic osteotome 90 includes a shank and an adjoined body 92. The body 92 having an apical end 94 remote from the shank. The body 92 is generally smooth (i.e., non-fluted) and has a conically tapered profile decreasing from a maximum diameter adjacent the shank to a minimum diameter adjacent the apical end 94. The overall proportion and dimensions of the body 92 will be similar to those of the body 42 in the preceding examples. The apical end 94 includes a unidirectional grinding formation that may take the form of a roughed surface. As the ultrasonic osteotome 90 is vibrated at a high frequency (as by a commercial off-the-shelf surgical ultrasonic generator) the apical end 94 has the effect of grinding some small portion of bone in a manner not too dissimilar from that of the apical end 48 in the earlier embodiments. The body 92 further includes an auto-grafting ramp 96 configured to auto-graft and compact bone after the bone has been ultrasonically pulverized by the apical end 94 as the body is forcibly advanced into an osteotomy concurrently with high-frequency vibration. In this example, the auto-grafting ramp 96 is a frusto-conical member disposed immediately below the smooth tapered portion of the body 92. The auto-grafting ramp 96 extends at a first angle that is larger than the taper of the body 92 so that the granular bone debris will be packed into the surrounding walls of the osteotomy with wedge-like action.

Figure 27A:
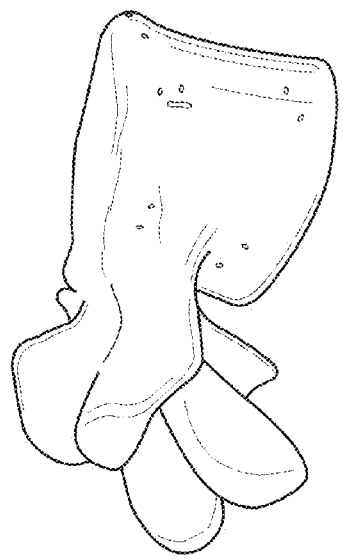
FIG. 27A is an enlarged view of a human vertebrae.
Figure 27B:
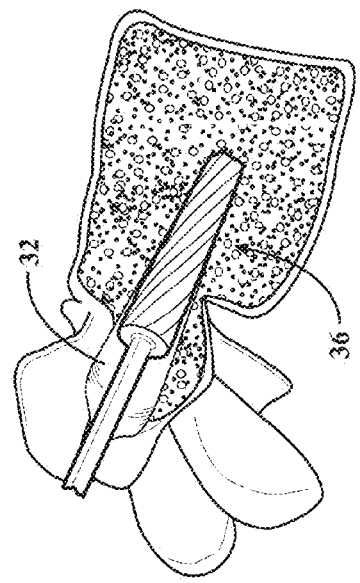
FIG. 27B is a view of the vertebrae as in FIG. 27A shown in cross-section with a rotary osteotome according to one embodiment of this invention disposed to enlarge an osteotomy for the purpose of receiving a fixation screw or other implant device.
Figure 27:
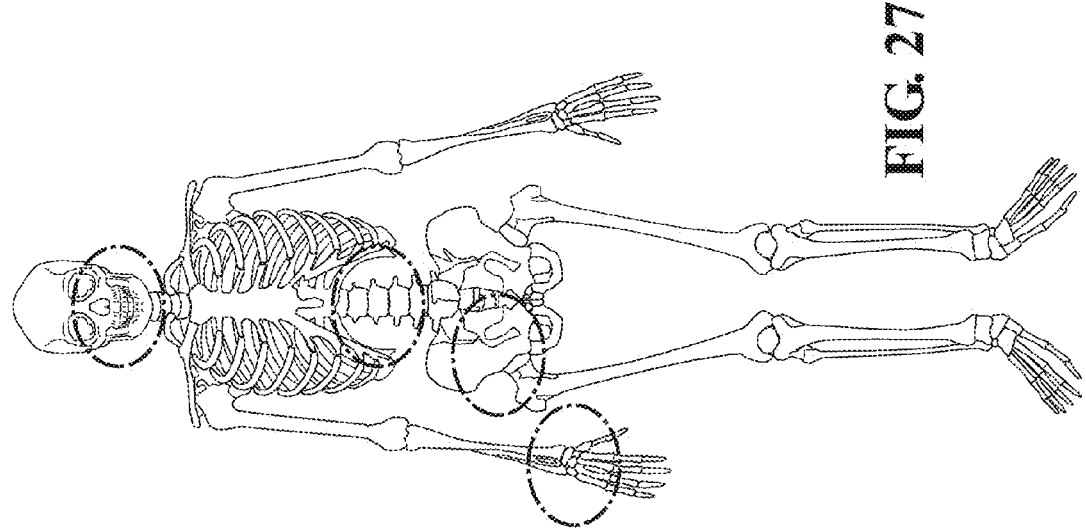
FIG. 27 is a simplified depiction of a human skeleton highlighting some examples of areas in which the novel osteotome of this invention might be effectively applied.

FIGS. 27-27B are intended to illustrate, for the benefit of the skilled artisan, that the principles of this invention are not limited to dental applications, but any bone preparation site within the human (or animal) body may be investigated for suitability. Initial indications reveal that applications in the vertebrae and hand/wrist are prime candidates for the bone burnishing techniques of this invention due to its potential for universally applicable increases in implant primary stability, auto-grafting benefits, and inherent similarity to prior art preparation techniques.

Figure 28:
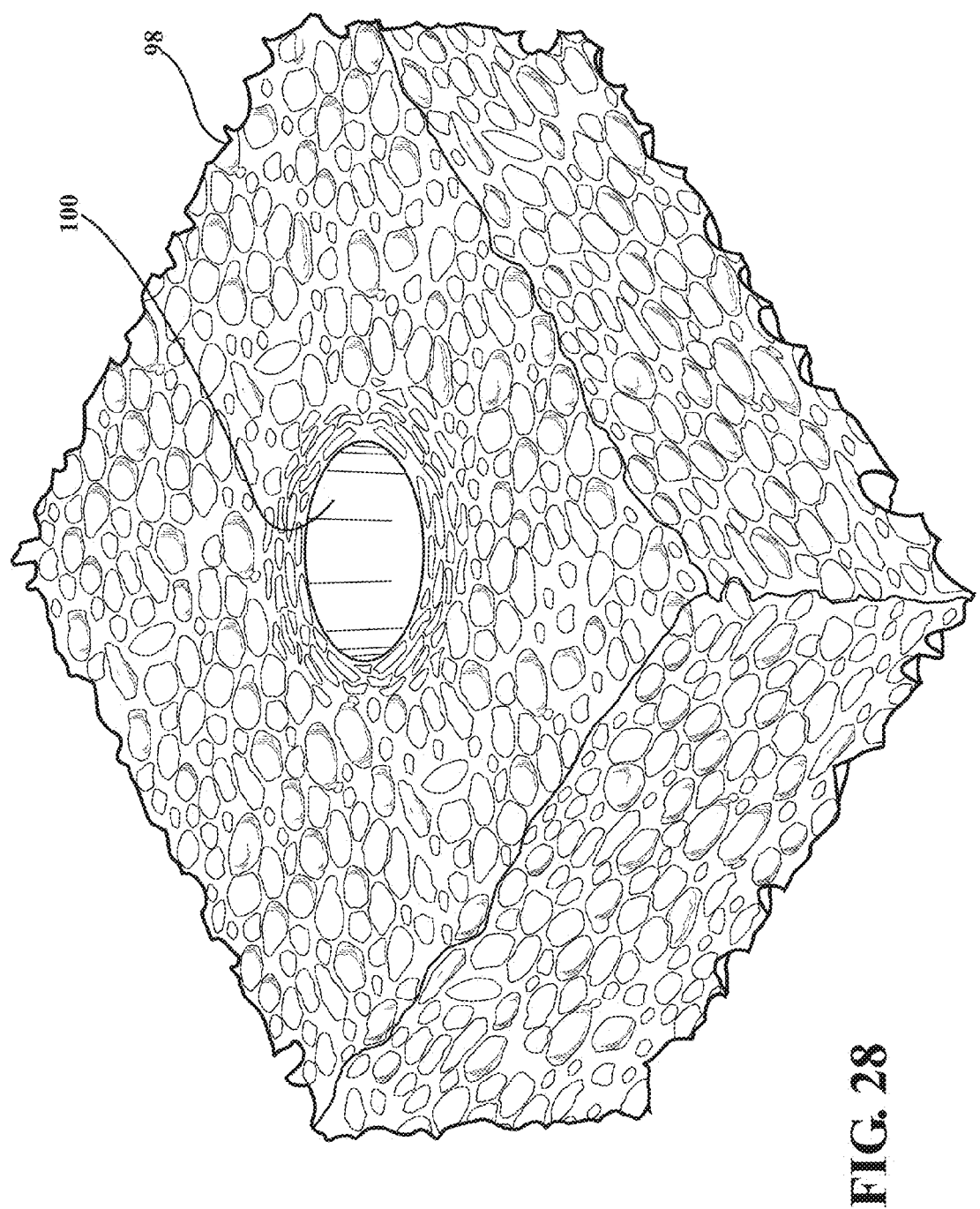
FIG. 28 is a perspective view of a foam metal product having a hole formed therein using a rotary osteotome according to this invention exemplifying at least one non-bone commercial application.

Furthermore, as shown in FIG. 28 the principles of this invention are not limited to bone as the host material. Indeed, the rotary tool 36 of this invention may be configured to enlarge a hole in almost any type of cellular material by burnishing. In this illustration, a section of metal foam 98 may be of the type used extensively in aerospace, heat shielding and other critical applications. The foam metal is shown including a hole 100 formed by burnishing according to the methods described above. The resulting hole 100 is better prepared to receive a screw or other fixation anchor because its inner walls have been densified by the compressive displacement and auto-grafting effects of this invention. Some experimentation has been made as well with hole formation in non-cellular inorganic materials like plate aluminum and plastic. Certain benefits have presented as well in these non-cellular materials, such that the potential to improve screw or anchor retention by hole preparation using the principles of this invention are fully contemplated.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A rotary osteotome (36) configured to be turned continuously at high speed in a non-cutting direction to enlarge an osteotomy (32), comprising:

a shank (40) establishing a longitudinal axis (A) of rotation for said rotary osteotome (36), a body (42) extending from said shank (40), said body (42) having an apical end (48) remote from said shank (40) and a conically tapered profile decreasing from a maximum diameter adjacent said shank (40) to a minimum diameter adjacent said apical end (48), a plurality of helically spiraling flutes (62) disposed about said body (42), a plurality of lands, each said land formed between adjacent flutes (62), each said land having a working edge (72) helically twisting about said body (42) in a direction that turns away from the non-cutting direction as said conically tapered profile decreases in diameter, said working edges (72) configured to radially displace surrounding bone material through compaction when said osteotome (36) is pushed into an osteotomy (32) while being rotated in the high-speed non-cutting direction, said apical end (48) of said body (42) including at least one grinding lip (50) extending radially from adjacent said longitudinal axis (A) to one of said working edges (72), a radially outer portion of said grinding lip (50) configured to grind bone material as said body (42) advances into the osteotomy (32) in the high-speed non-cutting direction, said grinding lip (50) having a generally planar first trailing flank (54), said first trailing flank (54) being canted from said grinding lip (50) at a first angle, a generally planar second trailing flank (56) falling away from said first trailing flank (54) at a second angle smaller than said first angle, a generally planar relief pocket (58) falling away from said second trailing flank (56) at a third angle smaller than said second angle, a plurality of said flutes (62) opening directly into said second trailing flank (56) to receive and then upwardly channel bone debris produced by said grinding lip (50) as said apical end (48) is pushed into the osteotomy (32) accompanied with high-speed rotation in the non-cutting direction, said working edges (72) further configured to auto-graft the bone debris particles channeled upwardly through said flutes (62) for repatriation into the surrounding bone material.

2. The rotary osteotome of claim 1, further including a generally axially disposed lip face (60) extending from said relief pocket (58), a plurality of said flutes (62) opening directly into said relief pocket (58) to receive bone debris produced by said grinding lip (50) as said apical end (48) is pushed into the osteotomy (32) accompanied with high-speed rotation in an opposite cutting direction.

3. The rotary osteotome of claim 1, wherein each said flute (62) has a burnishing face (64) and an opposing cutting face (66), and wherein each said land has a land face (70) joining a cutting face (66) of an adjacent said flute (62) at a respective one of said working edges (72) along a substantially marginless interface.

4. The rotary osteotome of claim 3, wherein said cutting face (66) establishes a rake angle relative to said longitudinal axis (A), wherein said rake angle is approximately zero degrees.

5. The rotary osteotome of claim 1, wherein said plurality of flutes (62) are equally circumferentially arranged about said body (42), said plurality of flutes (62) comprising at least four flutes (62).

6. The rotary osteotome of claim 1, wherein said body (42) has a conical taper between about 1° and 5° relative to said longitudinal axis (A).

7. The rotary osteotome of claim 1, wherein said flutes (62) have a helical spiral of about 9.5°, about 11°, about 12° or about 12.5°.

8. A rotary osteotome (36) configured to be turned continuously at high speed in a non-cutting direction to enlarge an osteotomy (32) by outward compaction of the surrounding bone material while concurrently auto-grafting particles of bone ground by the advancing apical end (48), said rotary osteotome (36) comprising:

a shank (40), said shank (40) establishing a longitudinal axis (A) of rotation for said rotary osteotome (36), a body (42) joined to said shank (40), said body (42) having an apical end (48) remote from said shank (40), said body (42) having a conically tapered profile decreasing from a maximum diameter adjacent said shank (40) to a minimum diameter adjacent said apical end (48), a plurality of helically spiraling flutes (62) disposed about said body (42), a plurality of lands, each said land formed between adjacent flutes (62), each said land having a working edge (72) helically twisting about said body (42) in a direction that turns away from the non-cutting direction as said conically tapered profile decreases in diameter, said working edges (72) configured to radially displace surrounding bone material through compaction when said osteotome (36) is pushed into an osteotomy (32) while being rotated in the high-speed non-cutting direction, said apical end (48) of said body (42) including a pair of substantially diametrically-opposed grinding lips (50), each said grinding lip (50) extending radially from adjacent said longitudinal axis (A) to a diametrically-opposed pair of said working edges (72), a radially outer portion of each said grinding lip (50) configured to grind bone material as said body (42) advances into the osteotomy (32) in the high-speed non-cutting direction, each said grinding lip (50) having a first trailing flank (54), said first trailing flank (54) being canted from the respective said grinding lip (50) at a first angle, each said grinding lip (50) having a second trailing flank (56) falling away from a respective one of said first trailing flanks (54) at a second angle smaller than said first angle, a relief pocket (58) falling away from each said second trailing flank (56) at a third angle smaller than said second angle, a plurality of said flutes (62) opening directly into each of said second trailing flanks (56) to receive and then upwardly channel bone debris produced by said grinding lip (50) as said apical end (48) is pushed into the osteotomy (32) accompanied with high-speed rotation in the non-cutting direction, said working edges (72) further configured to auto-graft the bone debris particles channeled upwardly through said flutes (62) for repatriation into the surrounding bone material.

9. The rotary osteotome of claim 8, further including a lip face (60) extending generally axially between each said relief pocket (58) and the adjacent said grinding lip (50), a plurality of said flutes (62) opening directly into said relief pocket (58) to receive bone debris produced by said grinding lip (50) as said apical end (48) is pushed into the osteotomy (32) accompanied with high-speed rotation in an opposite cutting direction.

10. The rotary osteotome of claim 8, wherein each said flute (62) has a burnishing face (64) and an opposing cutting face (66), and wherein each said land has a land face (70) joining a cutting face (66) of an adjacent said flute (62) at a respective one of said working edges (72) along a substantially margin-less interface.

11. The rotary osteotome of claim 10, wherein said cutting face (66) establishes a rake angle relative to said longitudinal axis (A), wherein said rake angle is approximately zero degrees.

12. The rotary osteotome of claim 8, wherein said plurality of flutes (62) are equally circumferentially arranged about said body (42), said plurality of flutes (62) comprising at least four flutes (62).

13. The rotary osteotome of claim 8, wherein said body (42) has a conical taper between about 1° and 5° relative to said longitudinal axis (A).

14. The rotary osteotome of claim 8, wherein said flutes (62) have a helical spiral of about 9.5°, about 11°, about 12° or about 12.5°.

15. The rotary osteotome of claim 8, wherein said pair of grinding lips (50) are offset from one another by an interposed chisel point (52), said chisel point (52) extending centrally through said longitudinal axis (A).

* * * * *